(12) United States Patent
Townsend et al.

(10) Patent No.: US 7,510,844 B2
(45) Date of Patent: Mar. 31, 2009

(54) CD86 AND CD80 RECEPTOR COMPETITION ASSAYS

(75) Inventors: Robert M. Townsend, Boothwyn, PA (US); Catherine A. Fleener, Holland, PA (US); Francisco Leon, Bethesda, MD (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/656,206

(22) Filed: Jan. 22, 2007

(65) Prior Publication Data

US 2007/0172895 A1 Jul. 26, 2007

Related U.S. Application Data

(60) Provisional application No. 60/761,624, filed on Jan. 24, 2006, provisional application No. 60/832,012, filed on Jul. 20, 2006.

(51) Int. Cl.
*G01N 33/53* (2006.01)

(52) U.S. Cl. ...................................... 435/7.1

(58) Field of Classification Search ................ None
See application file for complete search history.

(56) References Cited

U.S. PATENT DOCUMENTS

| | | | |
|---|---|---|---|
| 5,567,627 A | 10/1996 | Lehnen | |
| 5,844,095 A | 12/1998 | Linsley et al. | |
| 5,851,795 A | 12/1998 | Linsley et al. | |
| 5,885,796 A | 3/1999 | Linsley et al. | |
| 7,094,874 B2 * | 8/2006 | Peach et al. | 530/350 |
| 2002/0086414 A1 | 7/2002 | Freeman et al. | |
| 2002/0182211 A1 | 12/2002 | Peach et al. | |
| 2003/0224458 A1 | 12/2003 | Barber et al. | |
| 2004/0022787 A1 | 2/2004 | Cohen et al. | |

FOREIGN PATENT DOCUMENTS

| | | |
|---|---|---|
| WO | WO01/92337 A3 | 12/2001 |
| WO | WO02/094202 A2 | 11/2002 |

OTHER PUBLICATIONS

Lewandowski et al., J. Clin. Endocrinol. Metab., 1999, 84: 300-306.*
Townsend, R. et al., "Development of a whole blood CD86 receptor competition assay to measure receptor saturation by belatacept", American J. of Transplantation, vol. 6(2), pp. 698 (2006).
Wang, Q. et al., "Characterization and functional study of five novel monoclonal antibodies against human OX40L highlight reverse signaling: enhancement of IgG production of B cells and promotion of maturation of DCs", Tissue Antigens, vol. 64(5), pp. 566-574 (2004).
Carreno, B. et al., "The B7 Family of Ligands and its Receptors: New Pathways for costimulation and Inhibition of Immune Responses", Annu. Rev. Immunol., vol. 20, pp. 29-53 (2002).
Dinarello, C. et al., "Current Concepts Lymphokines", The New England Journal of Medicine, vol. 317(15), pp. 940-945 (1987).
Greene, J. et al., "Covalent Dimerization of CD28/CTLA-4 and Oligomerization of CD80/CD86 Regulate T Cell Costimulatory Interactions", The Journal of Biological Chemistry, vol. 271(43), pp. 26762-26771 (1996).
Hawrylowicz, C. et al., "Regulation of Antigen-Presentatoin-I IFN-γ Induces Antigen-Presenting Properties on B Cells", The Journal of Immunology, vol. 141(12), pp. 4083-4088 (1988).
Hemler, Martin., "Adhesive protein receptors on hematopoietic cells", Immunology Today, vol. 9(4), pp. 109-113 (1988).
Janeway, Jr. C.A., "Approaching the Asymptote? Evolution and Revolution in Immunology", Cold Spring Harbor Symposia on Quantitative Biology, vol. LIV, pp. 1-13 (1989).
Kakiuchi, T. et al., "B Cells as Antigen-Presenting Cells: The Requirement for B Cell Activation", The Journal of Immunology, vol. 131(1), pp. 109-114 (1983).
Krieger, J. et al., "Antigen Presentation by Splenic B Cells: Resting B Cells are Ineffective, whereas activated B Cells are effective accessory cells for T Cell responses", The Journal of Immunology, vol. 135(5), pp. 2937-2945 (1985).
Larsen, C. et al., "Rational Development of LEA29Y (belatacept), a High-Affinity Variant of CTLA4-lg with Potent Immunosuppressive Properties", American J. of Transplantation, vol. 5, pp. 443-453 (2005).
McKenzie, D., et al., "Alloantigen Presentation by B Cells, Requirement for IL-1 and IL-6", The J. of Immunology, vol. 141(9), pp. 2907-2911 (1988).
Salomon, B. et al., "Complexities of CD28/B7: CTLA-4 Costimulatory Pathways in Autoimmunity and Transplantation", Annual Rev. Immunology, vol. 19, pp. 225-252 (2001).
Shaw, S. et al., "Two molecular pathways of human T cell adhesion: establishment of receptor-ligand relationship", Current Opinion in Immunology, vol. 1, pp. 92-97 (1988).
Springer, T. et al., "The Lymphocyte Function-Associated LFA-1, CD2, and LFA-3 Molecules: Adhesion Receptors of the Immune System", Annual Review Immunology, vol. 5, pp. 223-252 (1987).
Weiss, A. et al., "The role of the T3/Antigen Receptor Complex in T-Cell Activation", Ann. Rev. Immunology, vol. 4, pp. 593-619 (1986).

* cited by examiner

*Primary Examiner*—Ilia Ouspenski
(74) *Attorney, Agent, or Firm*—Nickki L. Parlet

(57) ABSTRACT

The present invention discloses a method for assaying the binding of L104EA29YIg to a receptor. The receptor is preferably CD86 or CD80. The present invention also discloses antibodies to be used in the assay, as well as hybridomas expressing the antibodies.

23 Claims, 23 Drawing Sheets

```
 1       ↓
         ATG GGT GTA CTG CTC ACA CAG AGG ACG CTG
          M   G   V   L   L   T   Q   R   T   L
         └──→ Oncostatin M Signal Sequence →

41       CTC AGT CTG GTC CTT GCA CTC CTG TTT CCA AGC ATG GCG
          L   S   L   V   L   A   L   L   F   P   S   M   A

80       AGC ATG GCA ATG CAC GTG GCC CAG CCT GCT GTG GTA CTG
          S   M   A │ M   H   V   A   Q   P   A   V   V   L
                    └──→ Human CTLA4 →

119      GCC AGC AGC CGA GGC ATC GCC AGC TTT GTG TGT GAG TAT
          A   S   S   R   G   I   A   S   F   V   C   E   Y

158      GCA TCT CCA GGC AAA GCC ACT GAG GTC CGG GTG ACA GTG
          A   S   P   G   K   A   T   E   V   R   V   T   V

197      CTT CGG CAG GCT GAC AGC CAG GTG ACT GAA GTC TGT GCG
          L   R   Q   A   D   S   Q   V   T   E   V   C   A

236      GCA ACC TAC ATG ATG GGG AAT GAG TTG ACC TTC CTA GAT
          A   T   Y   M   M   G   N   E   L   T   F   L   D

275      GAT TCC ATC TGC ACG GGC ACC TCC AGT GGA AAT CAA GTG
          D   S   I   C   T   G   T   S   S   G   N   Q   V

314      AAC CTC ACT ATC CAA GGA CTG AGG GCC ATG GAC ACG GGA
          N   L   T   I   Q   G   L   R   A   M   D   T   G

353      CTC TAC ATC TGC AAG GTG GAG CTC ATG TAC CCA CCG CCA
          L   Y   I   C   K   V   E   L   M   Y   P   P   P

392      TAC TAC CTG GGC ATA GGC AAC GGA ACC CAG ATT TAT GTA
          Y   Y   L   G   I   G   N   G   T   Q   I   Y   V

431      ATT GAT CCA GAA CCG TGC CCA GAT TCT GAT CAG GAG CCC
          I   D   P   E   P   C   P   D   S   D   Q │ E   P
                                                    └──→

470      AAA TCT TCT GAC AAA ACT CAC ACA TCC CCA CCG TCC CCA
          K   S   S*  D   K   T   H   T   S*  P   P   S*  P
         Human IgG₁ Hinge →

509      GCA CCT GAA CTC CTG GGG GGA TCG TCA GTC TTC CTC TTC
          A │ P   E   L   L   G   G   S*  S   V   F   L   F
            └──→ Human IgG₁ Cʜ2 Domain →

548      CCC CCA AAA CCC AAG GAC ACC CTC ATG ATC TCC CGG ACC
          P   P   K   P   K   D   T   L   M   I   S   R   T
```

FIG. 3A

```
587  CCT GAG GTC ACA TGC GTG GTG GTG GAC GTG AGC CAC GAA
     P   E   V   T   C   V   V   V   D   V   S   H   E

626  GAC CCT GAG GTC AAG TTC AAC TGG TAC GTG GAC GGC GTG
     D   P   E   V   K   F   N   W   Y   V   D   G   V

665  GAG GTG CAT AAT GCC AAG ACA AAG CCG CGG GAG GAG CAG
     E   V   H   N   A   K   T   K   P   R   E   E   Q

704  TAC AAC AGC ACG TAC CGT GTG GTC AGC GTC CTC ACC GTC
     Y   N   S   T   Y   R   V   V   S   V   L   T   V

743  CTG CAC CAG GAC TGG CTG AAT GGC AAG GAG TAC AAG TGC
     L   H   Q   D   W   L   N   G   K   E   Y   K   C

782  AAG GTC TCC AAC AAA GCC CTC CCA GCC CCC ATC GAG AAA
     K   V   S   N   K   A   L   P   A   P   I   E   K

821  ACC ATC TCC AAA GCC AAA GGG CAG CCC CGA GAA CCA CAG
     T   I   S   K   A   K   G   Q   P   R   E   P   Q
                                →  Human IgG₁ C_H3 Domain →

860  GTG TAC ACC CTG CCC CCA TCC CGG GAT GAG CTG ACC AAG
     V   Y   T   L   P   P   S   R   D   E   L   T   K

899  AAC CAG GTC AGC CTG ACC TGC CTG GTC AAA GGC TTC TAT
     N   Q   V   S   L   T   C   L   V   K   G   F   Y

938  CCC AGC GAC ATC GCC GTG GAG TGG GAG AGC AAT GGG CAG
     P   S   D   I   A   V   E   W   E   S   N   G   Q

977  CCG GAG AAC AAC TAC AAG ACC ACG CCT CCC GTG CTG GAC
     P   E   N   N   Y   K   T   T   P   P   V   L   D

1016 TCC GAC GGC TCC TTC TTC CTC TAC AGC AAG CTC ACC GTG
     S   D   G   S   F   F   L   Y   S   K   L   T   V

1055 GAC AAG AGC AGG TGG CAG CAG GGG AAC GTC TTC TCA TGC
     D   K   S   R   W   Q   Q   G   N   V   F   S   C

1094 TCC GTG ATG CAT GAG GCT CTG CAC AAC CAC TAC ACG CAG
     S   V   M   H   E   A   L   H   N   H   Y   T   Q

1133 AAG AGC CTC TCC CTG TCT CCG GGT AAA TGA
     K   S   L   S   L   S   P   G   K   -
```

FIG. 3B

```
ATGGGTGTACTGCTCACACAGAGGACGCTGCTCAGTCTGGTCCTTGCACTCCTGTTTCCA      -19
M---G---V---L---L---T---Q---R---T---L---L---S---L---V---L---A---L---L---F---P--   -7

AGCATGGCGAGCATGGCAATGCACGTGGCCCAGCCTGCTGTGGTACTGGCCAGCAGCCGA      +42
S---M---A---S---M---A---M---H---V---A---Q---P---A---V---V---L---A---S---S---R--  +14
                +1

GGCATCGCTAGCTTTGTGTGTGAGTATGCATCTCCAGGCAAATATACTGAGGTCCGGGTG     +102
G---I---A---S---F---V---C---E---Y---A---S---P---G---K---Y---T---E---V---R---V--  +34

ACAGTGCTTCGGCAGGCTGACAGCCAGGTGACTGAAGTCTGTGCGGCAACCTACATGATG     +162
T---V---L---R---Q---A---D---S---Q---V---T---E---V---C---A---A---T---Y---M---M--  +54

GGGAATGAGTTGACCTTCCTAGATGATTCCATCTGCACGGGCACCTCCAGTGGAAATCAA     +222
G---N---E---L---T---F---L---D---D---S---I---C---T---G---T---S---S---G---N---Q--  +74

GTGAACCTCACTATCCAAGGACTGAGGGCCATGGACACGGGACTCTACATCTGCAAGGTG     +282
V---N---L---T---I---Q---G---L---R---A---M---D---T---G---L---Y---I---C---K---V--  +94

GAGCTCATGTACCCACCGCCATACTACGAGGGCATAGGCAACGGAACCCAGATTTATGTA     +342
E---L---M---Y---P---P---P---Y---Y---E---G---I---G---N---G---T---Q---I---Y---V-- +114

ATTGATCCAGAACCGTGCCCAGATTCTGATCAGGAGCCCAAATCTTCTGACAAAACTCAC     +402
I---D---P---E---P---C---P---D---S---D---Q---E---P---K---S---S---D---K---T---H-- +134

ACATCCCCACCGTCCCCAGCACCTGAACTCCTGGGGGGATCGTCAGTCTTCCTCTTCCCC     +462
T---S---P---P---S---P---A---P---E---L---L---G---G---S---S---V---F---L---F---P-- +154

CCAAAACCCAAGGACACCCTCATGATCTCCCGGACCCCTGAGGTCACATGCGTGGTGGTG     +522
P---K---P---K---D---T---L---M---I---S---R---T---P---E---V---T---C---V---V---V-- +174

GACGTGAGCCACGAAGACCCTGAGGTCAAGTTCAACTGGTACGTGGACGGCGTGGAGGTG     +582
D---V---S---H---E---D---P---E---V---K---F---N---W---Y---V---D---G---V---E---V-- +194

CATAATGCCAAGACAAAGCCGCGGGAGGAGCAGTACAACAGCACGTACCGTGTGGTCAGC     +642
H---N---A---K---T---K---P---R---E---E---Q---Y---N---S---T---Y---R---V---V---S-- +214

GTCCTCACCGTCCTGCACCAGGACTGGCTGAATGGCAAGGAGTACAAGTGCAAGGTCTCC     +702
V---L---T---V---L---H---Q---D---W---L---N---G---K---E---Y---K---C---K---V---S-- +234

AACAAAGCCCTCCCAGCCCCCATCGAGAAAACCATCTCCAAAGCCAAAGGGCAGCCCCGA     +762
N---K---A---L---P---A---P---I---E---K---T---I---S---K---A---K---G---Q---P---R-- +254

GAACCACAGGTGTACACCCTGCCCCCATCCCGGGATGAGCTGACCAAGAACCAGGTCAGC     +822
E---P---Q---V---Y---T---L---P---P---S---R---D---E---L---T---K---N---Q---V---S-- +274

CTGACCTGCCTGGTCAAAGGCTTCTATCCCAGCGACATCGCCGTGGAGTGGGAGAGCAAT     +882
L---T---C---L---V---K---G---F---Y---P---S---D---I---A---V---E---W---E---S---N-- +294

GGGCAGCCGGAGAACAACTACAAGACCACGCCTCCCGTGCTGGACTCCGACGGCTCCTTC     +942
G---Q---P---E---N---N---Y---K---T---T---P---P---V---L---D---S---D---G---S---F-- +314

TTCCTCTACAGCAAGCTCACCGTGGACAAGAGCAGGTGGCAGCAGGGGAACGTCTTCTCA    +1002
F---L---Y---S---K---L---T---V---D---K---S---R---W---Q---Q---G---N---V---F---S-- +334

TGCTCCGTGATGCATGAGGCTCTGCACAACCACTACACGCAGAAGAGCCTCTCCCTGTCT    +1062
C---S---V---M---H---E---A---L---H---N---H---Y---T---Q---K---S---L---S---L---S-- +354

CCGGGTAAATGA
P---G---K---*
```

Characterization of CD86 Competition in NHV Whole Blood Following *Ex Vivo* L104EA29YIg Ex

Figure 7

Characterization of CD86 Competition in NHV Whole Blood Following *Ex Vivo* L104EA29YIg Exposure Anti-CD86 mAB HA5.2B7 (1.25ug/ml)

| Donor# | BKGND MFI /NS | TOTAL MFI | ΔMFI / SPECIFIC | IC50 µg/ml | % INHIB @ 2 µg/ml | % INHIB @ 5 µg/ml |
|---|---|---|---|---|---|---|
| 101 | 11 | 51 | 40 | 0.13 | 75 | 81 |
| 173 | 9 | 39 | 30 | 0.08 | 77 | 82 |
| 003 | 11 | 48 | 37 | 0.02 | 88 | 92 |
| 183 | 12 | 44 | 31 | 0.09 | 83 | 89 |
| 122 | 16 | 71 | 55 | 0.01 | 91 | 94 |
| 190 | 13 | 82 | 69 | 0.01 | 90 | 93 |
| AVG | 12 | 56 | 44 | 0.06 | 84 | 89 |
| SD | 2.4 | 16.9 | 15.3 | 0.05 | 6.8 | 5.7 |
| RANGE | 9–16 | 39–82 | 30–69 | 0.01–0.13 | 75–91 | 81–94 |

• L104EA29YIg potency in an *in vitro* MLR: IC50 – 0.2ug/ml; IC90 – 3-10ug/ml

CD86 AND CD80 RECEPTOR COMPETITION ASSAYS

CROSS REFERENCE TO OTHER APPLICATIONS

This application claims the benefit of priority from provisional U.S. Patent Application 60/761,624, filed Jan. 24, 2006, and provisional U.S. Patent Application 60/832,012, filed Jul. 20, 2006.

FIELD OF THE INVENTION

The present invention relates to methods for monitoring compounds used to treat immune system diseases such as graft rejection following organ transplant. Specifically, the present invention relates to a flow-cytometry based CD86 or CD80 receptor competition based assay for measuring the binding efficiency of L104EA29YIg to CD86 or CD80 receptors by comparing the binding of non-competing anti-CD86 or CD80 monoclonal antibodies to CD86 or CD80 receptors (total CD86 or CD80 expression) respectively and the binding of competing anti-CD86 or CD80 antibodies to CD86 or CD80 receptors not bound by L104EA29YIg.

BACKGROUND OF THE INVENTION

The hallmark of a vertebrate immune system is the ability to discriminate "self" from "non-self" (foreign). This property has led to the evolution of a system requiring multiple signals to achieve optimal immune activation (Janeway, Cold Spring Harbor Symp. Quant. Biol. 54:1-14 (1989)). T cell-B cell interactions are essential to the immune response. Levels of many cohesive molecules found on T cells and B cells increase during an immune response (Springer et al., A. Rev. Immunol. 5:223-252 (1987); Shaw and Shimuzu, Current Opinion in Immunology, Eds. Kindt and Long, 1:92-97 (1988)); and Hemler Immunology Today 9:109-113 (1988)). Increased levels of these molecules may help explain why activated B cells are more effective at stimulating antigen-specific T cell proliferation than are resting B cells (Kaiuchi et al., J. Immunol. 131:109-114 (1983); Kreiger et al., J. Immunol. 135:2937-2945 (1985); McKenzie, J. Immunol. 141: 2907-2911 (1988); and Hawrylowicz and Unanue, J. Immunol. 141:4083-4088 (1988)).

The generation of a T lymphocyte ("T cell") immune response is a complex process involving cell-cell interactions (Springer et al., A. Rev. Immunol. 5:223-252 (1987)), particularly between T and accessory cells such as B cells, and production of soluble immune mediators (cytokines or lymphokines) (Dinarello and Mier, New Engl. Jour. Med 317: 940-945 (1987)). This response is regulated by several T-cell surface receptors, including the T-cell receptor complex (Weiss et al., Ann. Rev. Immunol. 4:593-619 (1986)) and other "accessory" surface molecules (Springer et al., (1987) supra). Many of these accessory molecules are naturally occurring cell surface differentiation (CD) antigens defined by the reactivity of monoclonal antibodies on the surface of cells (McMichael, Ed., Leukocyte Typing III, Oxford Univ. Press, Oxford, N.Y. (1987)).

In order to achieve effective T lymphocyte activation, two receptors on the cell surface must be engaged by their respective ligands and deliver a signal to the cell. First the T cell receptor must recognize antigen in the context of MHC on an antigen presenting cell. Second, a co-stimulatory receptor must bind the appropriate ligand, or co-receptor, on the antigen presenting cell. The most studied T cell co-stimulatory receptor is CD28, which binds to B7 molecules (CD80 and CD86) on antigen presenting cells. Green J L, Leytze G M, Emswiler J, Peach R, Bajorath J, Cosand W, Linsley P S. Covalent dimerization of CD28/CTLA-4 and oligomerization of CD80/CD86 regulate T cell costimulatory interactions. J. of Biol. Chem. 271: 26762-26771, 1994. Inhibition of the CD28/B7 pathway in vitro inhibits T cell proliferation, cytokine production and induces antigen specific T cell unresponsiveness. Green J L, Leytze G M, Emswiler J, Peach R, Bajorath J, Cosand W, Linsley P S. Covalent dimerization of CD28/CTLA-4 and oligomerization of CD80/CD86 regulate T cell costimulatory interactions. J. of Biol. Chem. 271: 26762-26771, 1994; and Kelly S, Linsley P, Warner G, Shyu W C and Paborji M. Investigator Brochure, BMS-188667, CTLA4Ig. In animal models, this pathway has been shown to be important in T cell-dependent immune responses, including alloantigen recognition and autoimmunity. Green J L, Leytze G M, Emswiler J, Peach R, Bajorath J, Cosand W, Linsley P S. Covalent dimerization of CD28/CTLA-4 and oligomerization of CD80/CD86 regulate T cell costimulatory interactions. J. of Biol. Chem. 271:26762-26771, 1994; and Kelly S, Linsley P, Warner G, Shyu W C and Paborji M. Investigator Brochure, BMS-188667, CTLA4Ig. Larsen, C. P., Pearson, T. C., Adams, A. B., Tso, P., Shirasugi, N., Strobert, E., Anderson, D., Cowan, S., Price, K., Naemura, J., Emswiler, J., Greene, J., Turk, L., Bajorath, J., Townsend, R., Hagerty, D., Linsley, P. S., and R. J. Peach. 2005. Rational Development of LEA29Y, a High-Affinity Variant of CTLA4-Ig with Potent Immunosuppressive Properties. *American Journal of Transplantation.* 5(3):443-53. Thus, the CD28/B7 pathway represents a viable, logical target for an immunomodulatory therapeutic agent.

CTLA4Ig (BMS-188667), a fusion protein comprising the extracellular domain of human CTLA-4 (cytotoxic T-lymphocyte-associated antigen 4) and a fragment of the Fc domain of human IgG1, blocks the CD28/B7 pathway by binding to CD80 and CD86 on the surface of the antigen presenting cells. This compound has been found to be clinically useful as an immunosuppressant. See U.S. patent application Ser. No. 10/419,008 (Publication No. 20040022787 A1), hereby incorporated by reference in its entirety, which describes and discusses CTLA4Ig and L104EA29YIg and methods of preparation and use thereof. U.S. Pat. Nos. 5,844, 095, 5,885,796, and 5,851,795, also incorporated by reference in their entirety, describe and discuss CTLA4Ig.

A related molecule, L104EA29YIg (BMS-224818) (also known as LEA29Y), was found to be a particularly potent immunomodulatory therapeutic agent. This compound is a human CTLA4Ig molecule containing a two amino acid substitution that results in enhanced binding to CD80 and CD86 relative to CTLA4Ig. See Larsen, C. P., Pearson, T. C., Adams, A. B., Tso, P., Shirasugi, N., Strobert, E., Anderson, D., Cowan, S., Price, K., NaemurFfia, J., Emswiler, J., Greene, J., Turk, L., Bajorath, J., Townsend, R., Hagerty, D., Linsley, P. S., and R. J. Peach. 2005. Rational Development of LEA29Y, a High-Affinity Variant of CTLA4-Ig with Potent Immunosuppressive Properties. *American Journal of Transplantation.* 5(3):443-53. U.S. patent application Ser. No. 09/865,321 (Publication No. 2002-0182211 A1), which is also hereby incorporated by reference in its entirety, describes and discusses L104EA29YIg.

CD80 and CD86 are discussed in Carreno, B. M., and Collins, M., 2002 (The B7 Family of Ligands and Its Receptors. New Pathways for Costimulation and Inhibition of Immune Responses, *Annu. Rev Immunol.* 20:29-53) and Salomon, B., and Bluestone, J. A., 2001 (Complexities of CD28/B7: CTLA-4 Costimulatory Pathways in Autoimmunity and Transplantation, *Annu. Rev. Immunol.* 19:225-52). Given that CTLA4Ig and L104EA29YIg bind to circulating leucocytes expressing CD80 and/or CD86 molecules, it would be informative to monitor the extent to which CD80 and/or CD86 is bound to the fusion protein(s), in addition to the amount of compound circulating in the plasma during clinical use. In doing so, clinicians would be able to correlate compound exposure levels with receptor saturation levels required for efficacy in order to monitor binding efficiency. Understanding the extent to which CD86 is saturated with L104EA29YIg at various blood concentrations can be used to help justify different dosing schemes or regimes. For example, during the development phase, different formulations and routes of administration will be utilized (e.g. monthly intravenous or weekly subcutaneous treatment). This assay could be used to help establish the best route and course of administration which demonstrates maximum saturation for the longest period of time.

BRIEF SUMMARY OF THE INVENTION

The present invention relates to assays for monitoring and measuring the binding of L104EA29YIg to a receptor, in particular, a CD86 or CD80 receptor. In this assay, peripheral mononuclear cells are isolated from a blood sample, and portions of the mononuclear cell sample are preincubated with increasing concentrations of L104EA29YIg. After incubation, a labeled anti-CD86 or anti-CD80 antibody is added, and the binding of the labeled antibody is measured using flow cytometry. By comparing the binding of portions of the mononuclear cell sample with varying concentrations of L104EA29YIg added to a portion of the mononuclear cell sample with no L104EA29YIg added, one can determine that L104EA29YIg is binding the receptor.

In yet another embodiment of the invention, an assay method is provided in which the binding efficiency of L104EA29YIg to a receptor is measured using a competing antibody and a non-competing antibody concurrently. In such an assay, peripheral monocytes are isolated from a blood sample, and portions of the monocyte sample are preincubated with L104EA29YIg. After incubation, a labeled competing anti-receptor antibody is added, and then a non-competing anti-receptor antibody is added. The binding of the two antibodies is measured using flow cytometry. The binding of the non-competing antibody represents the amount of total receptor, and the binding of the competing antibody represents the amount of available receptor, unbound by L104EA29YIg. In this way, the binding efficiency of L104EA29YIg may be determined using a single sample.

In yet another embodiment of the invention, an assay method is provided in which the binding efficiency of L104EA29YIg to a receptor is measured using a competing antibody and a non-competing antibody in separate samples. In such an assay, whole blood is treated with L104EA29YIg. PBS is used as an untreated control. Mouse IgG solution is added to all samples to block non-specific binding of detection reagents. To detect levels of unbound CD86, fluorescently labeled competing anti-receptor antibody (e.g., mAb HA5) is added to one set of samples. To detect total CD86 levels, a fluorescently labeled non-competing anti-receptor antibody (e.g. mAb 2D4) is added to another set of samples. To detect monocytes, CD14-FITC is added to each sample. To assess non-specific fluorescence associated with the labeled anti-CD86 mAbs, excess unlabeled anti-human CD86 mAb is added to a subset of the relevant samples (e.g. unlabeled HA5 is added to samples containing labeled HA5). Cells are lysed using Lysing solution, and the binding of the antibodies is measured using flow cytometry. The binding of the non-competing antibody represents the amount of total receptor, and the binding of the competing antibody represents the amount of available receptor, unbound by L104EA29YIg. Specific binding (ΔMFI (Medium fluorescence intensity)) is determined by the difference between the total binding (labeled anti-CD86 mAb alone) and the non-specific binding (labeled + excess unlabeled anti-CD86 mAb). In this way, the binding efficiency of L104EA29YIg may be determined using two separate samples.

In yet another embodiment of the invention, an assay method is provided for monitoring the binding efficiency of L104EA29YIg in a clinical setting. In such an assay, a patient is dosed with L104EA29YIg. A blood sample from the patient is obtained, and a mixture of mouse IgGs are added to aliquots of the blood sample to reduce Fc receptor-mediated non-specific binding. Human CD14-FITC is added to identify monocytes. Then, labeled competing anti-receptor antibody and labeled non-competing anti-receptor antibody are added to the aliquots of blood sample. As above, to assess non-specific fluorescence associated with the labeled anti-CD86 mAbs, excess unlabeled anti-human CD86 mAb is added to a subset of the relevent samples (e.g. unlabeled HA5 is added to samples containing labeled HA5). A lysing/fixative solution is used to lyse red blood cells and fix leukocytes. The samples are centrifuged to remove lysed blood cells and isolate leukocytes. The total receptor and available receptor (not bound by L104EA29YIg) are measured by determining the binding of the competing and non-competing antibodies (respectively). Specific binding (ΔMFI) is determined by the difference between the total binding (labeled anti-CD86 mAb alone) and the non-specific binding (labeled+excess unlabeled anti-CD86 mAb).

In one preferred aspect of the above embodiments of the present invention, the receptor is CD86 or CD80.

In another preferred aspect of the above embodiments, the anti-receptor antibody is an anti-CD86 antibody. In particular, the competing anti-CD86 antibody is FUN-1, IT2.2, or HA5 (clone HA5.2B7). In another preferred embodiment, the anti-receptor antibody is an anti-CD80 antibody. In particular, the competing anti-CD80 antibody is either mAb L307.4 or mAb MAB104.

In another preferred aspect of the invention, the anti-human CD86 or anti-human CD80 antibody is labeled with a fluorophore. In another preferred aspect of the invention, the fluorophore is phycoerythrin (PE).

In yet another preferred aspect of the above embodiments, the non-competing anti-CD86 antibody is mAb 2D4.

In yet another preferred aspect of the above embodiments, the non-competing anti-CD80 antibody is mAb 1420.

In yet another embodiment of the invention, monoclonal antibodies mAb 1420 and 2D4, and hybridomas that express such mAbs are provided. The hybridomas used to produce these antibodies were deposited on Jan. 13, 2006 with the American Type Culture Collection (ATCC), 10801 University Blvd., Manassas, Va. 20110-2209 under the provisions of the Budapest Treaty, and have been accorded ATCC accession number PTA-7304 (hybridoma expressing mAb 1420), and PTA-7305 (hybridoma expressing mAb 2D4). These and other embodiments of the invention will be apparent in light of the detailed description below.

BRIEF DESCRIPTION OF THE FIGURES

FIG. 3 presents the nucleotide sequence (SEQ ID NO:1) of the CTLA4Ig molecule. Also shown is the amino acid sequence (SEQ ID NO:2) encoded by the nucleic acid. CTLA4Ig molecules that can be produced from this nucleotide sequence include molecules having the amino acid sequence of residues: (i) 26-383 of SEQ ID NO:2, (ii) 26-382 of SEQ ID NO:2, (iii) 27-383 of SEQ ID NO:2, or (iv) 26-382 of SEQ ID NO:2, or optionally (v) 25-382 of SEQ ID NO:2, or (vi) 25-383 of SEQ ID NO:2. The DNA and amino acid sequences comprise the following regions: (a) an Oncostatin M signal sequence (amino acids 1-26 of SEQ ID NO:2); (b) an extracellular domain of human CTLA4 (amino acids 27-151 of SEQ ID NO:2); (c) a modified portion of the human IgG1 constant region (amino acids 152-383 of SEQ ID NO:2), including a modified hinge region (amino acids 152-166 of SEQ ID NO:2), a modified human IgG1 CH2 domain (amino acids 167-276 of SEQ ID NO:2), and a human IgG1 CH3 domain (amino acids 277-383 of SEQ ID NO:2).

FIG. 4 depicts a nucleotide (SEQ ID NO:3) and amino acid (SEQ ID NO:4) sequence of L104EA29YIg (also known as "LEA29Y") comprising an Oncostatin M signal sequence; a mutated extracellular domain of CTLA4 starting at (as designated in FIG. 4) methionine at position +1 and ending at aspartic acid at position +124, or starting at alanine at position −1 and ending at aspartic acid at position +124; and an Ig region. SEQ ID NO: 3 and 4 designate the first amino acid of the Oncostatin M signal sequence (M, which is followed by G) as 1. SEQ ID NO: 3 and 4 depict a nucleotide and amino acid sequence, respectively, of L104EA29YIg comprising an Oncostatin M signal sequence; a mutated extracellular domain of CTLA4 starting at methionine at position +27 and ending at aspartic acid at position +150, or starting at alanine at position +26 and ending at aspartic acid at position +150; and an Ig region. L104EA29YIg can have the amino acid sequence of residues: (i) 26-383 of SEQ ID NO:4, (ii) 26-382 of SEQ ID NO:4; (iii) 27-383 of SEQ ID NO:4 or (iv) 27-382 of SEQ ID NO:4, or optionally (v), 25-382 of SEQ ID NO:4, or (vi) 25-383 of SEQ ID NO:4.

FIG. 6 depicts the characterization of CD86 competition with mAb FUN1 after incubation of whole blood with L104EA29YIg. (MFI=Median fluorescence intensity; MLR=Mixed leukocyte reaction; NS=Non-specific). This figure summarizes FUN-1 performance in the assay on blood collected from 6 different NHVs demonstrating the effect of L104EA29YIg inhibition of antibody binding.

FIG. 7 depicts the characterization of CD86 competition with mAb HA5 after incubation of whole blood with L104EA29YIg. This figure summarizes HA5 performance in the assay on blood collected from 6 different NHVs demonstrating the effect of L104EA29YIg inhibition of antibody binding.

FIG. 8 demonstrates that L104EA29YIg administration SC to normal healthy volunteers, inhibits the binding of FUN1 to monocytes by day 5, but this effect is reversed by day 14.

DETAILED DESCRIPTION OF THE INVENTION

Figure 1:
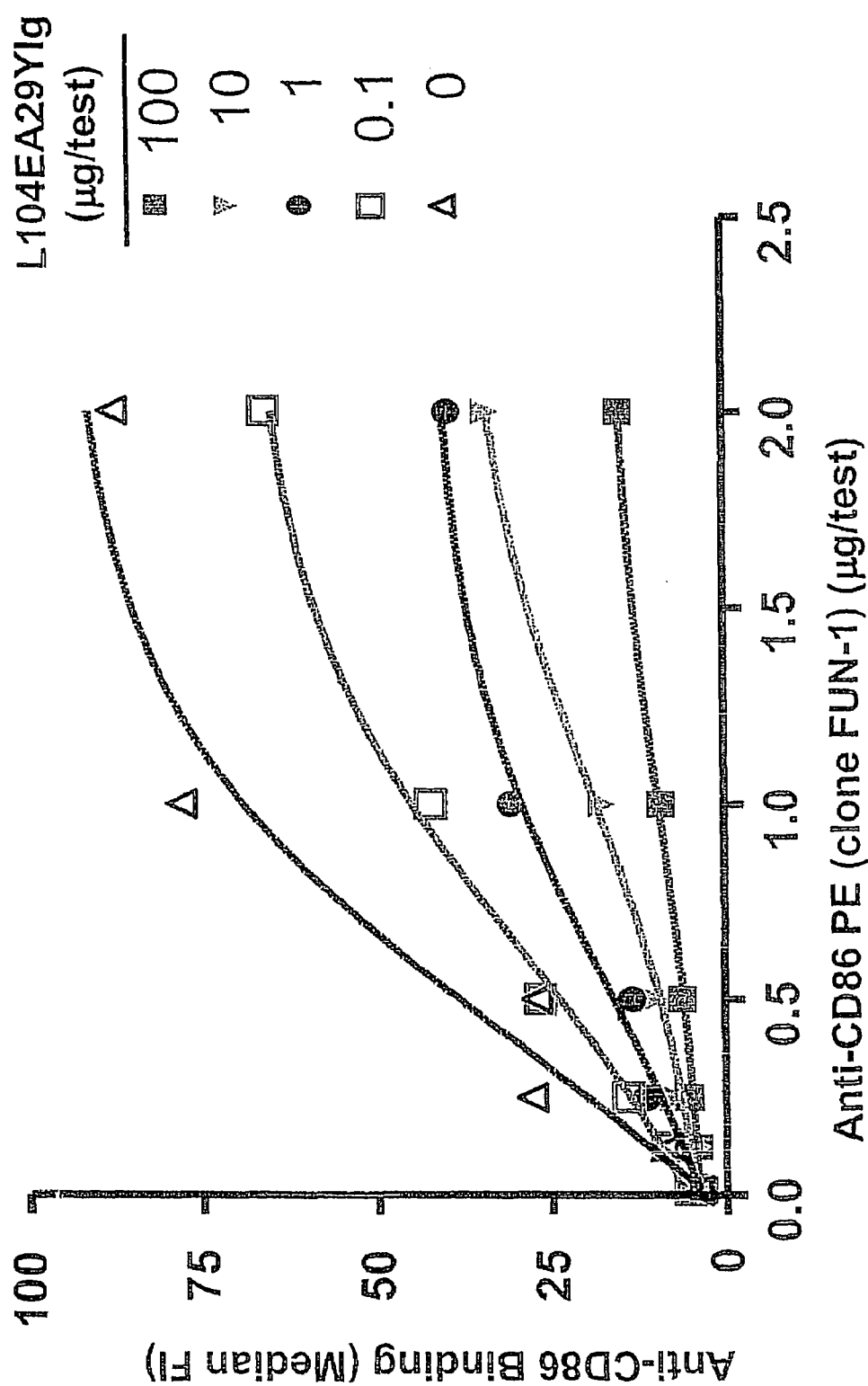
FIG. 1 illustrates the results of a CD86 competition in isolated peripheral blood mononuclear cells with competing mAb FUN-1.

The present invention may be understood more readily by reference to the following detailed description of the preferred embodiments of the invention and the Examples included herein. This invention describes the development of a flow cytometry-based "CD86 Receptor Competition Assay" for L104EA29YIg.

Preliminary attempts to develop a CTLA4Ig-based CD80 and/or CD86 receptor competition assay failed. Most peripheral blood monocytes express very low (or no) levels of CD80 on their surface prior to stimulation, thus developing a CD80 receptor competition assay would be highly challenging. Additionally, the relatively high affinity of L104EA29YIg for CD86 (relative to CTLA4Ig or mAbs) allows L104EA29YIg to compete for binding with the anti-CD86 mAbs tested.

Flow cytometry has been used with increasing regularity in clinical laboratories for immunophenotyping of leukocyte antigens. The advantages of flow cytometry include speed, sensitivity, precision and objectivity. The components and operation of flow cytometers is well known to those skilled in the art and will not be described in detail herein. For purposes of a description of such, applicants refer to U.S. Pat. No. 5,567,627, issued Oct. 22, 1996 which is incorporated herein by reference in its entirety. It is sufficient to indicate that the components and methodology of flow cytometry can be used to provide specific information on a number of parameters of a sample. For example it is possible to provide information on components of different sizes within a sample, while simultaneously providing information on signals of different wavelengths received from different components received from the sample. Thus, when a sample includes components of varying sizes and also includes components with labels which emit different wavelengths of light the flow cytometry data obtained can provide multidimensional information to the user. The present invention utilizes this technology by providing different types of labeled antibodies and labeled and unlabelled cells expressing known antigens. By exposing a sample to such and thereafter analyzing such within a flow cytometer it is possible to obtain substantial amounts of information regarding the blood in a quick and efficient manner.

In this flow cytometric assay, the total CD86 expression levels on peripheral monocytes are detected by a truly non-competing mAb (e.g. 2D4) and the level of CD86 molecules not bound by L104EA29YIg is detected by a competing anti-CD86 mAb (e.g. FUN-1 and IT2.2).

As used herein, a competing anti-receptor antibody is an antibody which is measurably prevented from binding to a receptor by a given molecule, such as L104EA29YIg. A non-competing anti-receptor antibody is an antibody which does not measurably prevent binding of a given molecule, such as L104EA29YIg, to the receptor.

As used herein, "CTLA4Ig" or "CTLA4-Ig" refers to a protein molecule having the amino acid sequence of residues: (i) 26-383 of SEQ ID NO:2, (ii) 26-382 of SEQ ID NO:2; (iii) 27-383 of SEQ ID NO:2, or (iv) 27-382 of SEQ ID NO:2, or optionally (v) 25-382 of SEQ ID NO:2, or (vi) 25-383 of SEQ ID NO:2. Expression of CTLA4Ig in mammalian cells can result in the production of N- and C- terminal variants. CTLA4Ig also refers to multimeric forms of the polypeptide, such as dimers, tetramers, and hexamers. Dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer CTLA4Ig molecules. (DNA encoding CTLA4Ig as shown in SEQ ID NO:2 was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; a Chinese Hamster Ovary (CHO) cell line expressing CTLA4Ig as shown in SEQ ID NO:2 was deposited on May 31, 1991 with ATCC identification number CRL-10762).

L104EA29YIg (also known as "LEA29Y" or "L104EA29Y") is a genetically engineered fusion protein similar in structure to CTAL4Ig. Two amino acid modifications were made to CTLA4Ig, leucine to glutamic acid at position 104 (L104E), which is position 130 of SEQ ID NO:2, and alanine to tyrosine at position 29 (A29Y), which is position 55 of SEQ ID NO:2, to generate L104EA29YIg.

As used herein, "L104EA29YIg" refers to a protein molecule having the amino acid sequence of residues: (i) 26-383 of SEQ ID NO:4, (ii) 26-382 of SEQ ID NO:4; (iii) 27-383 of SEQ ID NO:4, or (iv) 27-382 of SEQ ID NO:4, or optionally (v) 25-382 of SEQ ID NO:4, or (vi) 25-383 of SEQ ID NO:4. Expression of L104EA29YIg in mammalian cells can result in the production of N- and C- terminal variants. L104EA29YIg also refers to multimeric forms of the polypeptide, such as dimers, tetramers, and hexamers. Dimer combinations can include, for example: (i) and (i); (i) and (ii); (i) and (iii); (i) and (iv); (i) and (v); (i) and (vi); (ii) and (ii); (ii) and (iii); (ii) and (iv); (ii) and (v); (ii) and (vi); (iii) and (iii); (iii) and (iv); (iii) and (v); (iii) and (vi); (iv) and (iv); (iv) and (v); (iv) and (vi); (v) and (v); (v) and (vi); and, (vi) and (vi). These different dimer combinations can also associate with each other to form tetramer L104EA29YIg molecules. (DNA encoding L104EA29YIg was deposited on Jun. 20, 2000, with the American Type Culture Collection (ATCC) under the provisions of the Budapest Treaty. It has been accorded ATCC accession number PTA-2104. L104EA29YIg is further described in co-pending U.S. patent application Ser. Nos. 09/579,927, 60/287,576 and 60/214,065, and in US20020182211A1 and WO/01/923337A2, which are incorporated by reference herein in their entireties.)

EXAMPLES

Example 1

In Vitro Assays

Initial experiments were performed to measure the binding of L104EA29YIg to CD86. Various antibodies were used singly or in combination to develop an assay procedure that allows the measurement of L104EA29YIg binding relative to the availability of CD86 receptor.

Materials
- Dulbecco's PBS without Ca++ and Mg++ (Mediatech Inc., Herndon Va., Cat #21-031-CM), or equivalent
- BMS-224818-01 (L104EA29YIg), 100 mg, resuspended and stored frozen as a 10 mg/ml stock solution in PBS
- Lymphocyte Separation Medium (Mediatech Inc., Herndon Va., Cat #25-072-CV)
- Sodium azide (Sigma-Aldrich, Milwaukee, Wis., Cat #S2002), or equivalent
- Trypan Blue, 0.4% (Invitrogen, Grand island N.Y., Cat #15250-061) or equivalent
- 10×FACS Lysing Solution (BD Biosciences, San Jose Calif., Cat #349202)
- Fetal Bovine Serum (Mediatech Inc., Herndon Va., Cat #35-011-CV), or equivalent
- Human IgG1κ, from human plasma (Sigma-Aldrich, St. Louis, Mo., Cat #15154), or equivalent
- IgG from human serum (Sigma-Aldrich, St. Louis, Mo., Cat #14506), or equivalent
- IgG from murine serum (Sigma-Aldrich, St. Louis, Mo., Cat #15381), or equivalent
- Anti-CD14-FITC conjugated mAb (Becton Dickinson, San Jose, Calif. Cat #555397)
- Anti-CD86-PE conjugated mAb, clone FUN-1 (Becton Dickinson, San Jose, Calif. Cat #555658)
- Anti-CD86-PE conjugated mAb, clone IT2.2 (Becton Dickinson, San Jose, Calif. Cat #555665)
- Anti-CD86-PE conjugated mAb 2D4-PE. (BMS proprietary mAb, conjugated to PE, Batch Control #14640, by Caltag Laboratories)
- Anti-CD80-PE conjugated mAb (1420-PE) (BMS proprietary mAb, conjugated to PE, Batch Control #17312, by Caltag Laboratories.)
- Sodium citrate CPT Vacutainer™, 8 mL, (Becton Dickinson, Cat #362761)
- Sodium heparin CPT Vacutainer™, 8 mL, (Becton Dickinson, Cat #362753)
- Anti-CD80 conjugated mAb L307.4 (Becton Dickinson, Cat 340294)
- Anti-CD80 conjugated mAB 104 (Beckman Coulter, Cat #IM1976)
- Anticoagulant Acid Citrate Dextrose Solution Formula (ACD-A) (2 mg/ml dextrose, 1.8 mg/ml sodium citrate, 0.6 mg/ml citric acid; Gambro #777967000) Heparin (Sigma H3149, 30 U/ml)

A. Detection of CD86 in Human PBMC and Competition with L104EA29YIg

Given that monocytes represent the circulating leukocyte population expressing the most abundant expression of CD86, the expression of CD86 on CD14+ monocytes was evaluated in a two color direct immunofluorescence assay (FIG. 1). As expected, peripheral monocytes in PBMCs (peripheral blood monocytes) expressed moderate levels of CD86 as detected by anti-CD86 mAb FUN-1 (or IT2.2 data not shown) binding. When PBMCs are pre-incubated with increasing concentrations of L104EA29YIg (0.1 to 100 μg/test), the detectable anti-CD86 binding was inhibited in a concentration dependant manner. These data suggest that L104EA29YIg can compete with selective anti-CD86 mAbs (e.g. FUN-1 and IT2.2) for CD86 binding on peripheral blood monocytes. Thus the reagents and potential for generating a CD86 receptor competition assay to measure co-stimulation blockade by L104EA29YIg exists and does so only due to the unique high affinity L104EA29YIg has for CD86.

Not wishing to be bound by any specific procedure, the Applicants provide the following example procedure to demonstrate how the assay may be done in an in vitro setting:

PBMC Procedure:
1. 40 ml blood is drawn into a syringe containing heparin (30 U/ml), EDTA (5.4 mM) or ACD-A (2 mg/ml dextrose, 1.8 mg/ml sodium citrate, 0.6 mg/ml citric acid) as an anti-coagulant.
2. Layer 20 ml of blood over 15 ml of Lymphocyte Separation Medium.
3. Centrifuge 1800 rpm for 25 minutes at room temperature.
4. Remove the PBMC layer and transfer to a 50 ml tube. Add 30 ml PBS.
5. Centrifuge 1800 rpm for 10 minutes at room temperature.
6. Resuspend the pellet in 50 ml PBS.
7. Centrifuge at 1200 rpm for 10 minutes at room temperature.
8. Resuspend the pellet in PBS and determine cell number using trypan blue staining.
9. Resuspend the cells at a final concentration of $10^7$ cells per ml in 0.5% FBS/PBS/0.1% sodium azide.
10. Aliquot $10^6$ cells (100 μl) into a 12×75 mm polystyrene tube on ice.
11. Add L104EA29YIg at desired concentrations (e.g., between 0 and 200μg/ml) to tube and incubate for 15 minutes on ice.
12. Add 20 μg of either human IgG1 (200 μg/ml final concentration) or mixed human IgGs (200 μg/ml final concentration) to block potential FcR binding of detection antibodies. Incubate 10 minutes on ice.
13. Add indicated amount (e.g. 1 μg) of anti-human CD86 PE (antibody labeled with PE, i.e., phycoerythrin) (e.g. BD clone FUN1) antibody, incubate 30 minutes on ice
14. Add 1 ml FACS Lysing Solution, incubate 30 minutes on ice.
15. Centrifuge at 1500 rpm for 5 minutes at 4 C. Resuspend pellet in 250 ul FACS Lysing Solution.
16. Read on flow cytometer. For acquisition, gate on the monocyte population, as identified by forward and side scatter properties (G1). Acquisition is stopped after accumulation of 5000 G1 events.
17. For analysis, the median fluorescence of G1 events is determined on a histogram of FL2 events (CD86 PE) and is used to determine the relative level of CD86 present on the surface of monocytes.

B. Detection of CD86 in Human Whole Blood Samples and Competition with L104EA29YIg To be useful as a clinical assay, the CD86 competition observed on PBMC's must also be detectable in whole blood samples. To demonstrate this potential, whole blood from a normal healthy volunteer was drawn into vacutainers containing either ACD or EDTA. The blood was then pre-incubated with 0, 5, 120 and 250 µg/mL L104EA29YIg at 37° C. for 1 hour. Following incubation, CD86 not occupied by L104EA29YIg was measured by incubating the blood samples at 4° C. with FUN-1 (and/or IT2.2). The results of the flow cytometry measurements suggest that expected levels of CD86 expression on CD14+ monocytes were detected; however, the use of different anti-coagulants resulted in different levels of detectable CD86 in the absence of L104EA29YIg. Increasing concentrations of L104EA29YIg inhibited FUN-1 binding in a concentration dependant manner (FIG. 2a) and there appeared to be no effect of anticoagulant choice on this inhibition.

Not wishing to be bound by any specific procedure, the Applicants provide the following example procedure to demonstrate how the assay may be done:

Whole Blood Procedure
1. Draw blood into ACD-A anticoagulant
2. Dispense L104EA29YIg into 12×75 mm polypropylene tube for desired final concentration (e.g., between 0 and 200 µg/ml).
3. Add whole blood to L104EA29YIg. Incubate on a rotator in the 37° C. $CO_2$ incubator for 1 hr.
4. Aliquot 200 ul of blood sample into a 12×75 mm polystyrene tube on ice.
5. To each tube, add 25 ug of mouse mixed IgGs to block potential FcR binding of detection antibodies. Incubate for 15 minutes on ice.
6. To each tube, add 20 ul anti-human CD14 FITC (5 µg/ml)/ and indicated amount (e.g. 1 ug) of anti-human CD86 PE (e.g. BD clone FUN1). Incubate on ice for 30 minutes.
7. Add 2 ml of FACS Lysing Solution (BD) to each tube. Incubate on ice for 30 minutes.
8. Spin the tubes for 5 minutes at 1500 rpm, at 4° C.
9. Resuspend in 200 µl FACS Lysing Solution.
10. Read on flow cytometer, adjusting compensation settings as necessary. For acquisition, gate on the monocyte population, as identified by forward and side scatter properties (G1). Gate on CD14+ monocytes using a dot plot of forward scatter vs. CD14 (G2). The additive events of G1 and G2 (termed G3) are observed on a histogram looking at the FL2 channel (CD86 PE). Acquisition is stopped after accumulation of 3000 G3 events.
11. For analysis, the median fluorescence of G3 events is determined on a histogram of FL2 events (CD86 PE) and is used to determine the relative level of CD86 present on the surface of CD14+ monocytes.

C. Detection of CD86 in Human Whole Blood Cells with Concurrent use of Competing and Non-Competing Anti-CD86 Antibodies.

Figure 2A:
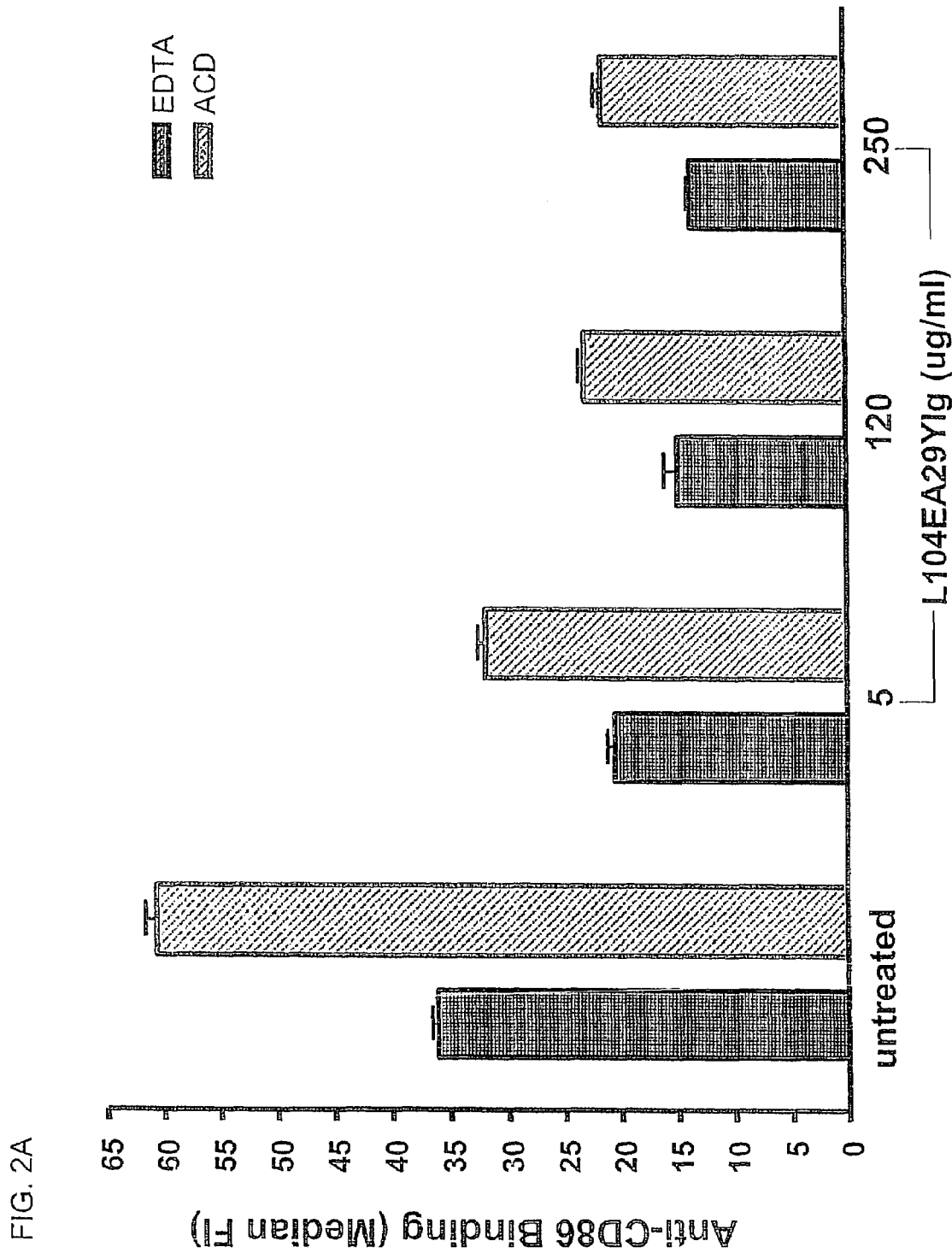
FIG. 2 illustrates (a) the results of competition in whole blood with competing mAb FUN-1 (1 ug/ml) and (b) the results of competition in whole blood with a non-competing mAb 2D4.
Figure 2B:
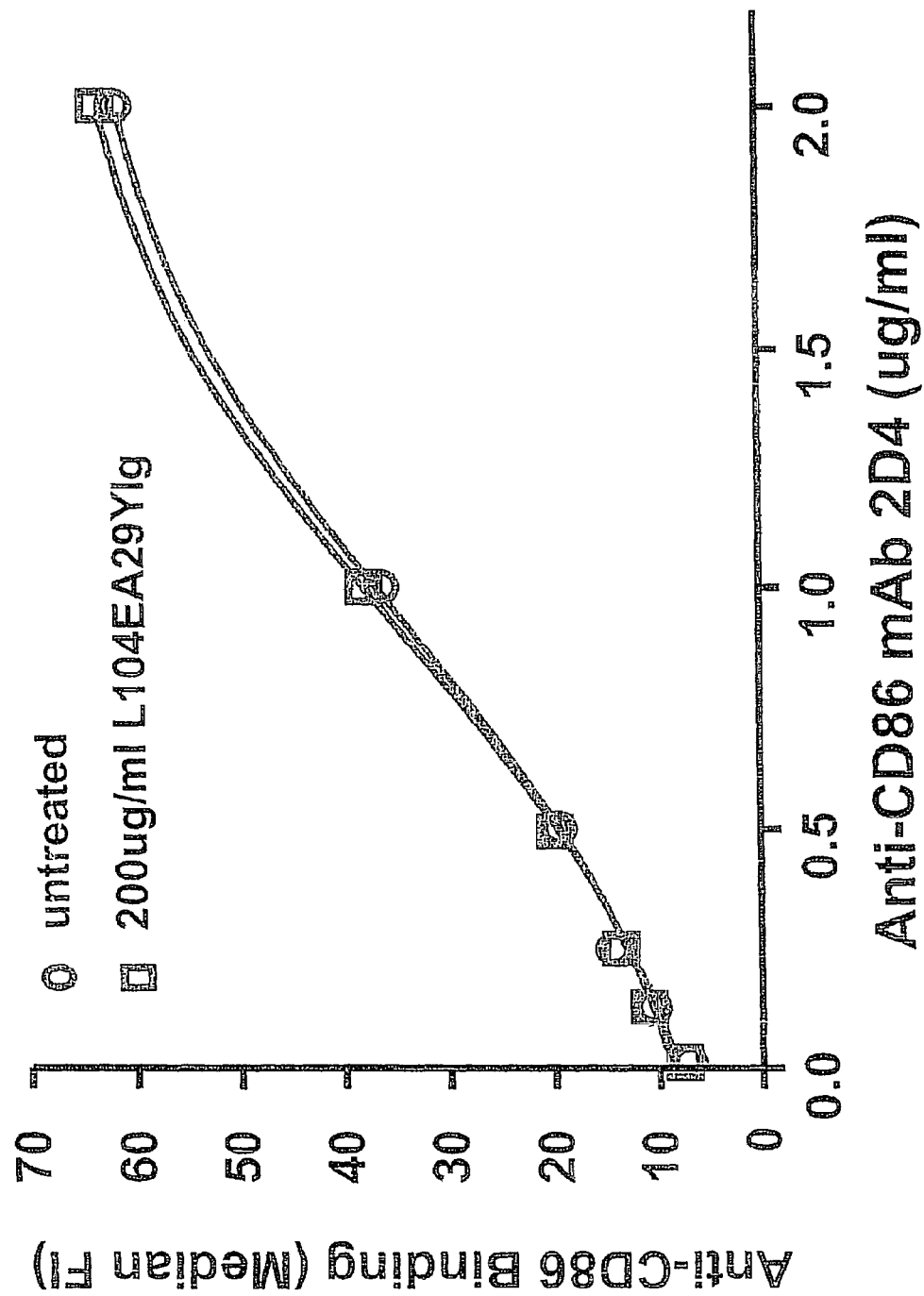

Additionally, the binding of 2D4, an anti-CD86 mAb which does not compete with CTLA-4, is not affected by the preincubation with a high concentration (200 µg/ml) of L104EA29YIg (FIG. 2b). This suggests that 2D4 does not compete with L104EA29YIg for binding to CD86 and can be used to measure the total surface expression of CD86 even in the presence of L104EA29YIg.

D. Summary

The data for these experiments are shown in FIGS. 1, 2a and 2b. These data demonstrate that selected anti-CD86 mAbs (e.g. FUN-1 and IT2.2), which do not compete with CTLA4Ig, will compete with L104EA29YIg for binding to CD86 on the surface of antigen presenting cells. The data also demonstrate that truely non competing anti-CD86 mAbs (e.g. 2D4) can be used to measure total surface CD86 expression even in the presence of high concentrations of L104EA29YIg. These observations are unique to L104EA29YIg due to the enhanced affinity for CD86 as compared to CTLA4Ig and other CD86 ligands. These observations are the basis for the novel application of these reagents for the development of a clinical assay to measure costimulation blockade by L104EA29YIg.

Example 2

Clinical Ex Vivo and In Vivo Studies

Figure 5:
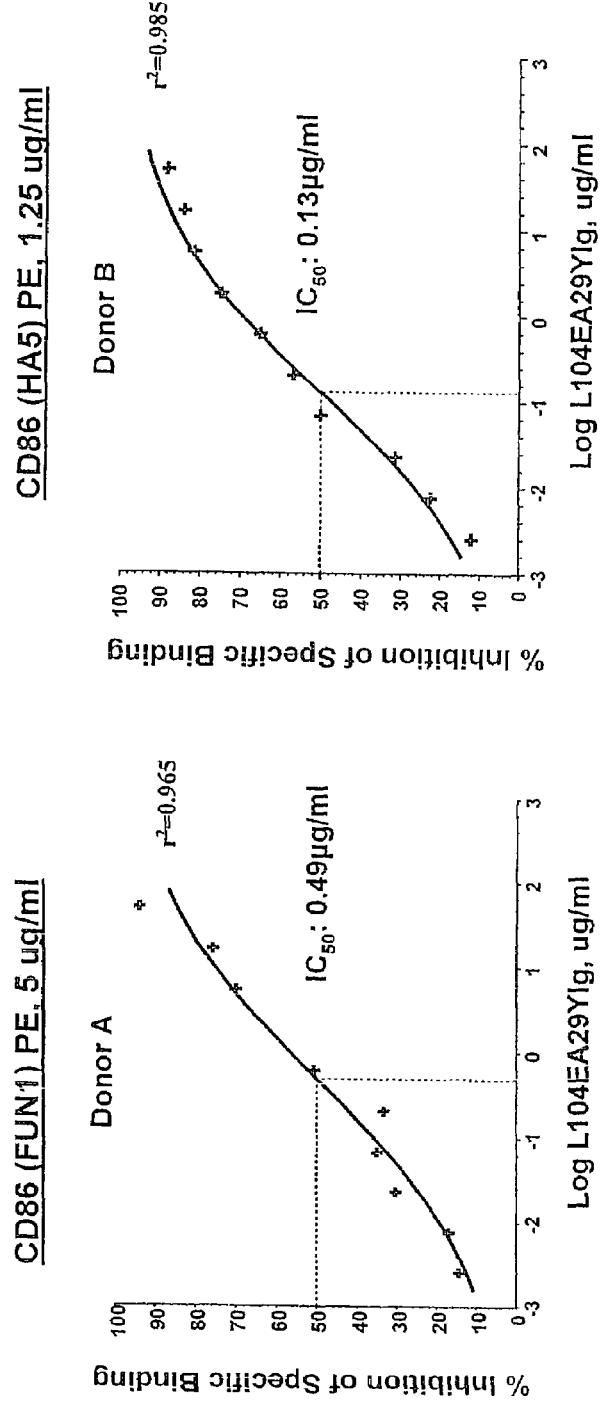
FIG. 5 depicts the results of an ex vivo CD86 receptor competition in whole blood with mAb HA5 and mAb FUN1. (NHV=Normal healthy volunteer.) This figure demonstrates that the concentration of L104EA29YIg required to inhibit specific binding of HA5 by 50% is 0.13 ug/ml, and the concentration of L104EA29YIg required to inhibit the specific binding of FUN1 by 50% is 0.49 ug/ml.
Figure 10:
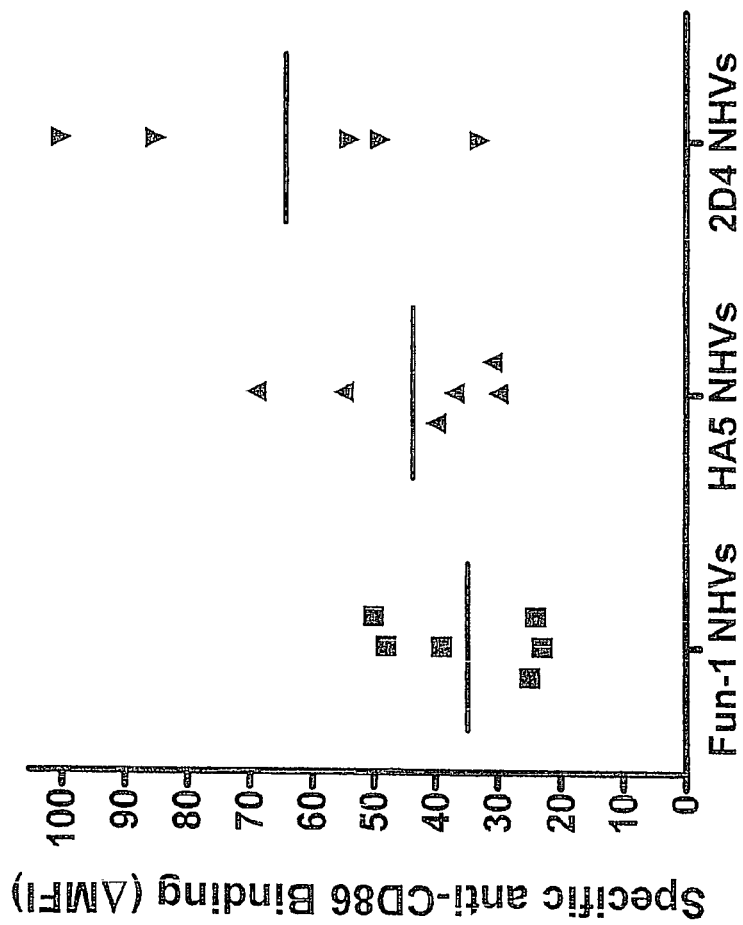
FIG. 10 depicts a comparison of the specific binding of several anti-CD86 mAbs in NHVs to monocytes in whole blood. The data show that all three antibodies bind to monocytes in a similar fashion.
Figure 14:
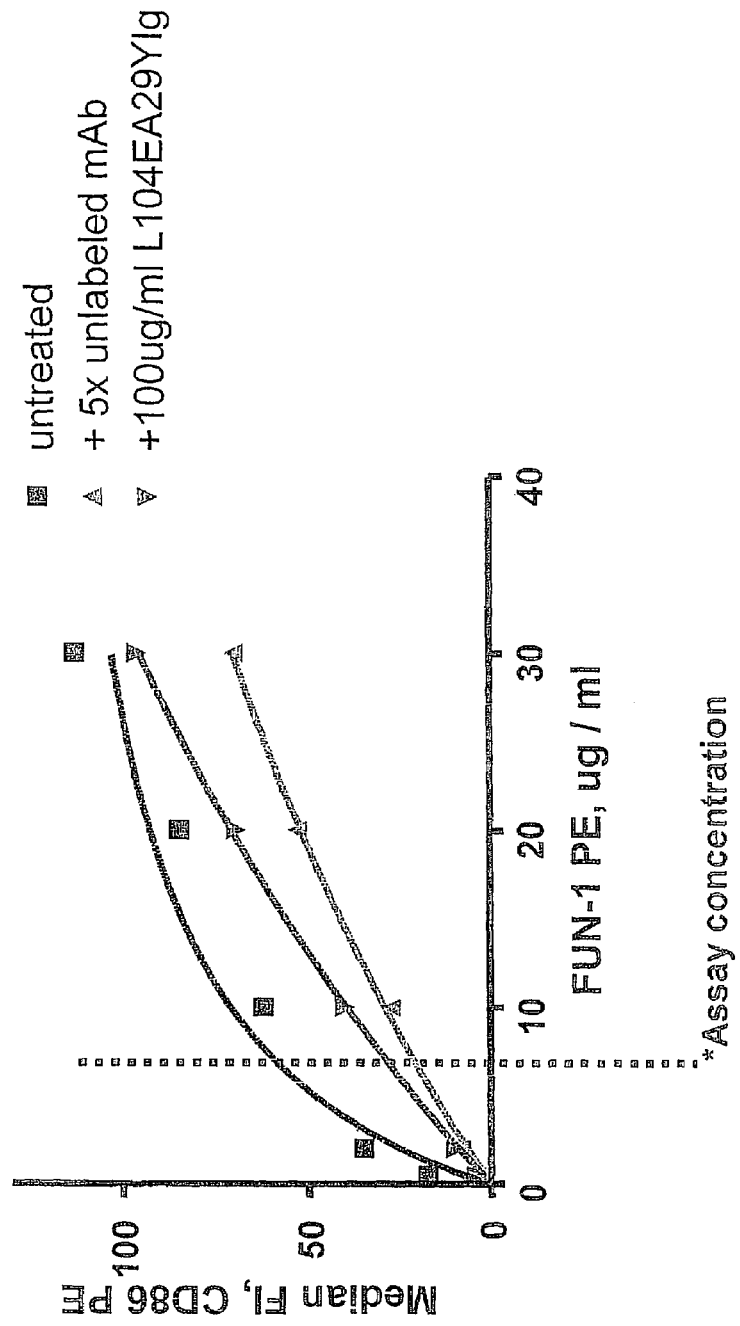
FIG. 14 depicts the titration of anti-CD86 PE FUN1, demonstrating the effects on L104EA29YIg binding. These results were used to determine the concentration of antibodies to use in competition assays.
Figure 15:
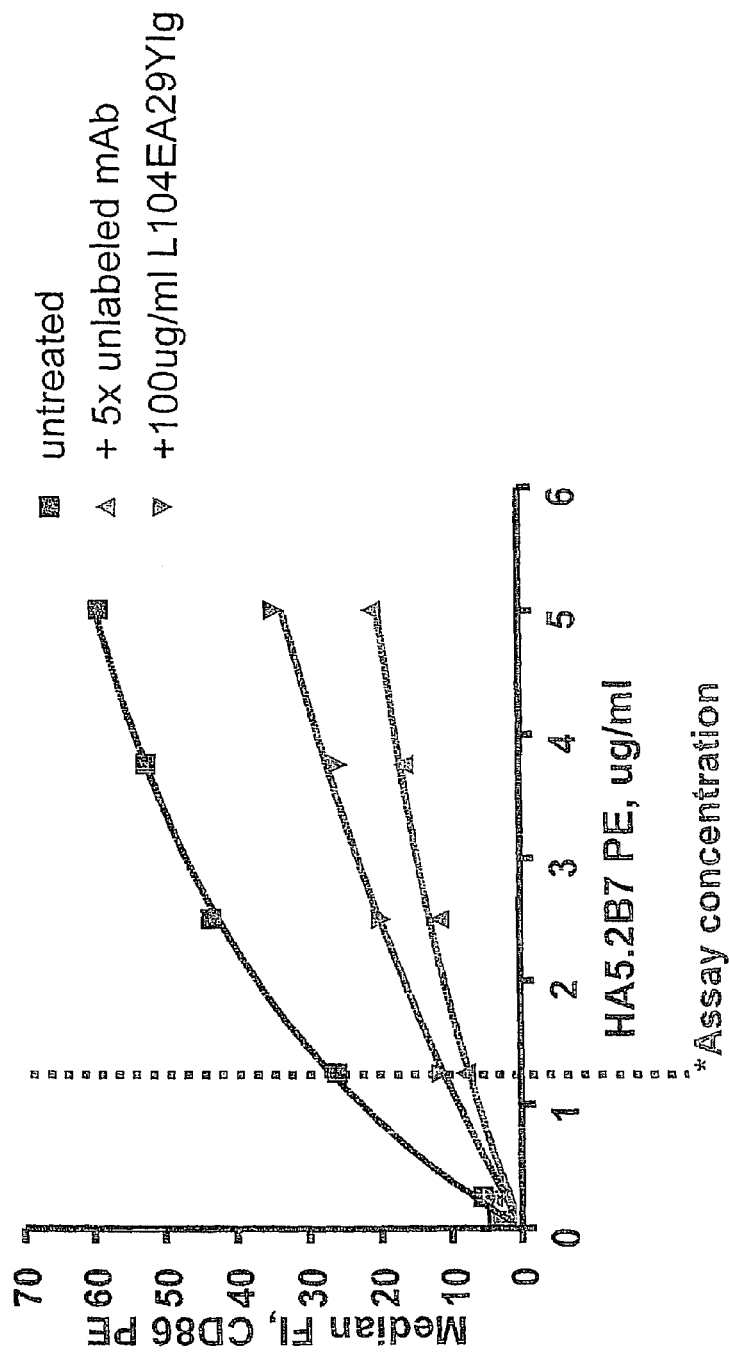
FIG. 15 depicts the titration of anti-CD86 PE HA5.2B7, demonstrating the effects on L104EA29YIg binding. These results were used to determine the concentration of antibodies to use in competition assays.
Figure 16:
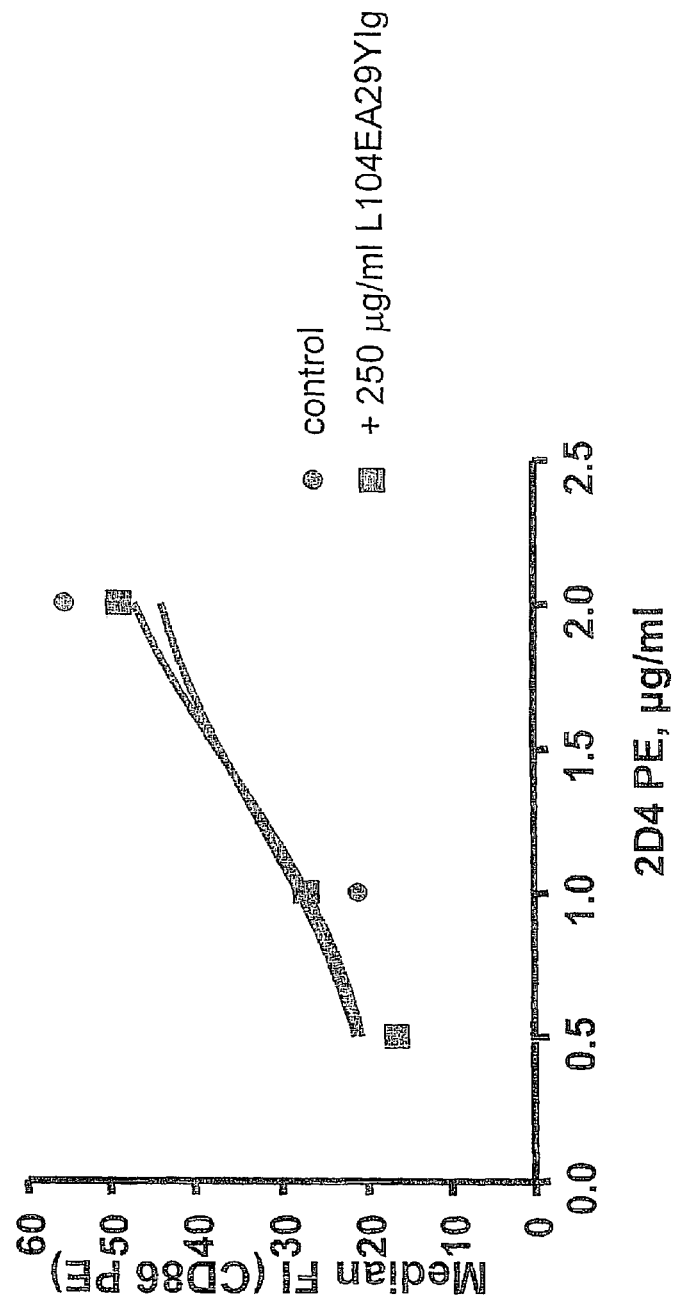
FIG. 16 depicts the titration of anti-CD86 PE 2D4, demonstrating the effects of L104EA29YIg binding. L104EA29YIg does not affect the binding of mAb 2D4.
Figure 17:
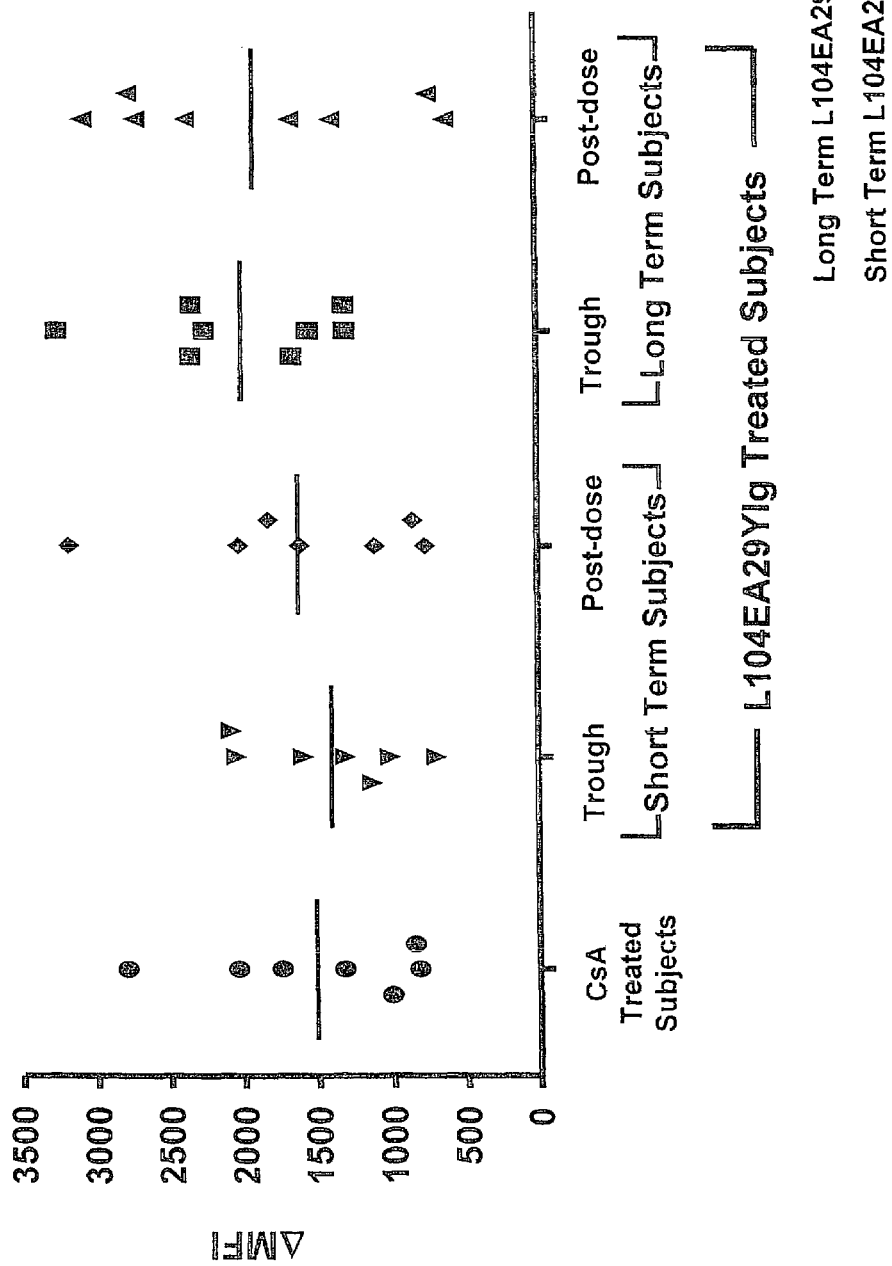
FIG. 17 depicts specific binding of a non-competing mAb 2D4 in clinical samples of long term and short term subjects. In transplant patient receiving L104EA29YIg, 2D4 binding is unchanged following administration of L104EA29YIg and not significantly different from Cyclosporine A (CsA) treated control subjects. The assay is similar to the assay described in FIG. 11 except that CsA treated subjects are used as controls and results from subjects treated with L104EA29YIg for a period of 6 months or less are also included.
Figure 18:
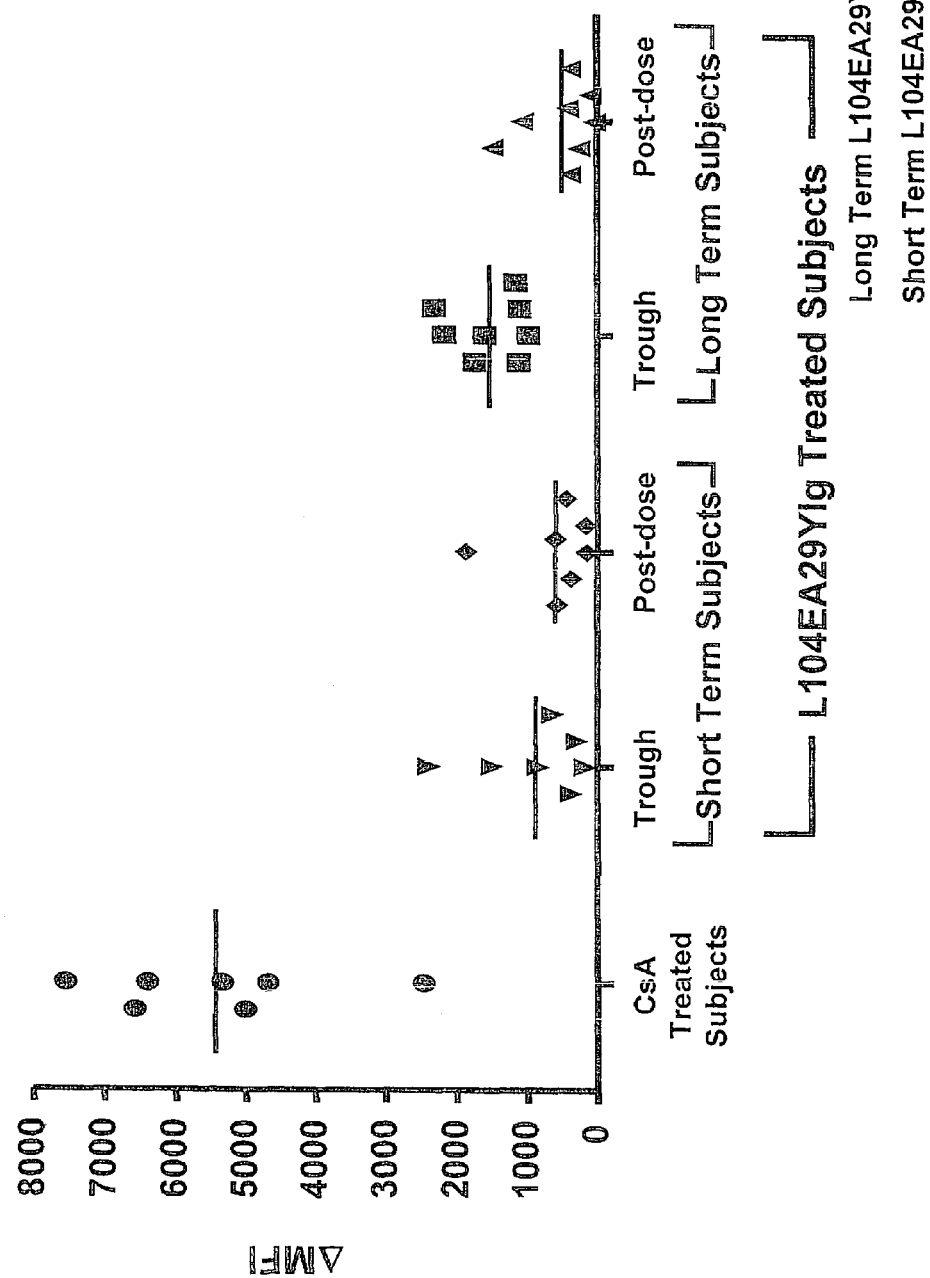
FIG. 18 depicts specific binding of a competing monoclonal antibody HA5 in clinical samples of long term and short term subjects. This data demonstrate that HA5 binding is significantly inhibited by L104EA29YIg administration in transplant patients and significantly reduced compared to CsA treated control subjects. The assay is similar to the assay described in FIG. 12 except that CsA treated subjects were used as controls and results from subjects treated with L104EA29YIg for a period of 6 months or less are also included.
Figure 19:
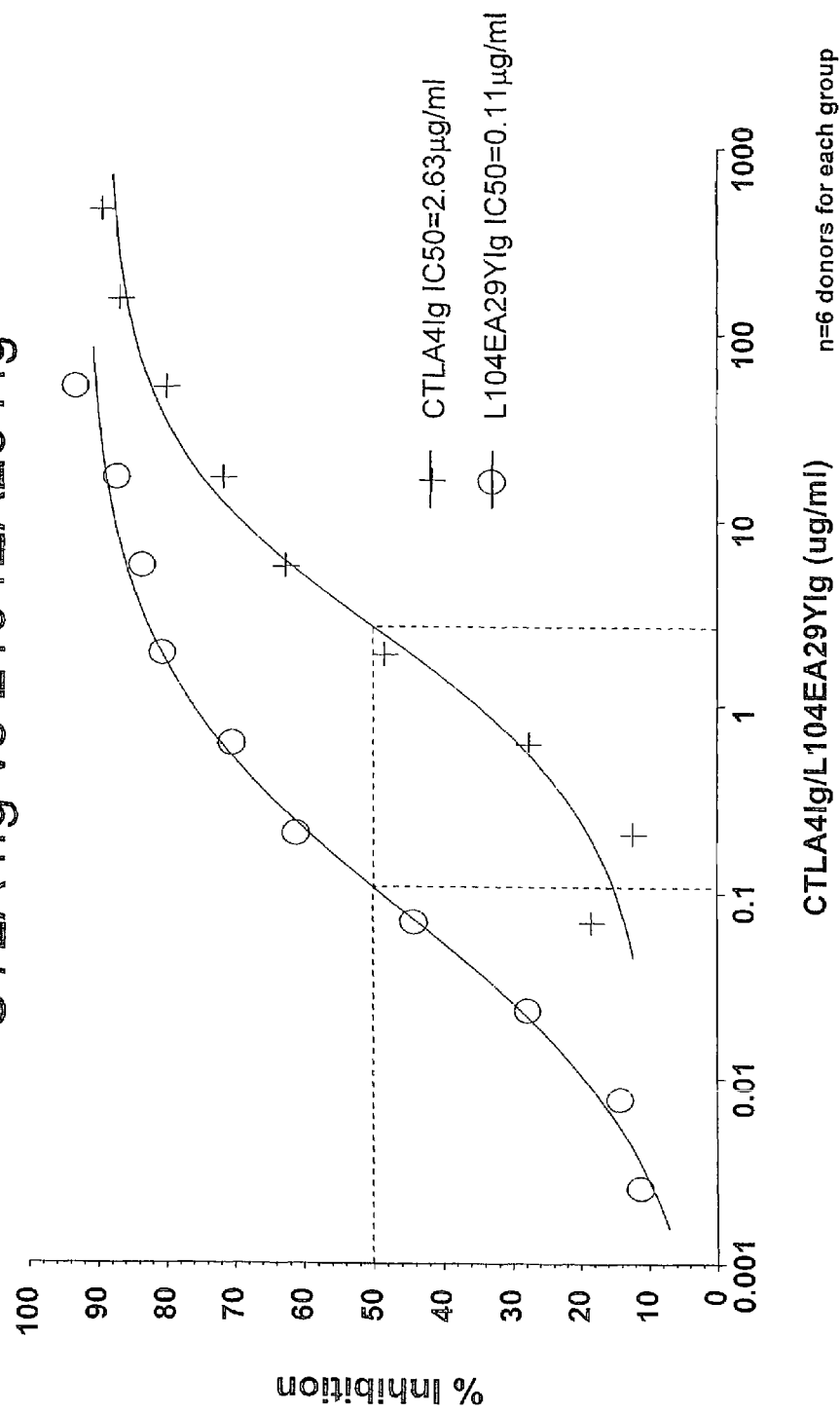
FIG. 19 depicts CD86 receptor competition assay in whole blood from normal healthy volunteers with mAb HA5. The data demonstrates that the concentration of CTLA4Ig required to inhibit specific binding of HA5 by 50% is 2.63 μg/ml, whereas the concentration of L104EA29YIg required to inhibit specific binding of HA5 by 50% is 0.11 μg/ml. The assay is the same type of assay as shown in FIG. 5, donor B, except that the results in FIG. 19 represent the average response of 6 donors.

To be useful as a clinical assay, the CD86 competition observed on PBMC's must also be detectable in whole blood samples. To demonstrate this potential, whole blood from a normal healthy volunteer was drawn into vacutainers containing either ACD or EDTA. The blood was then pre-incubated with varying concentrations of L104EA29YIg. Assay concentrations were determined by titration of FUN-1 PE, HA5 PE and 2D4 PE. (See FIGS. 14-16, and Tables 1 and 2). Following incubation, CD86 not occupied by L104EA29YIg was measured by incubating the blood samples at 4° C. with HA5.2B7. The concentration of L104EA29YIg required to inhibit antibody binding by 50% varies, depending on the antibody. For example, 0.13 µg/ml of L104EA29YIg is required to inhibit HA5 binding by 50%, while 0.49 µg/ml of L104EA29YIg is required to inhibit FUN-1 binding by 50%. (See FIG. 5). FUN-1 and HA5 performance in the assay on blood collected from 6 different normal healthy volunteers (NHVs) demonstrating the effect of L104EA29YIg inhibition of antibody binding is shown in FIGS. 6 and 7. In general, HA5 appears to be more sensitive as it detects greater receptor saturation at similar L104EA29YIg concentrations and lower IC50s. All three monoclonal antibodies (FUN-1, HA5, and 2D4) bind to CD86 (on monocytes) at similar levels. (See FIG. 10).

Figure 8:
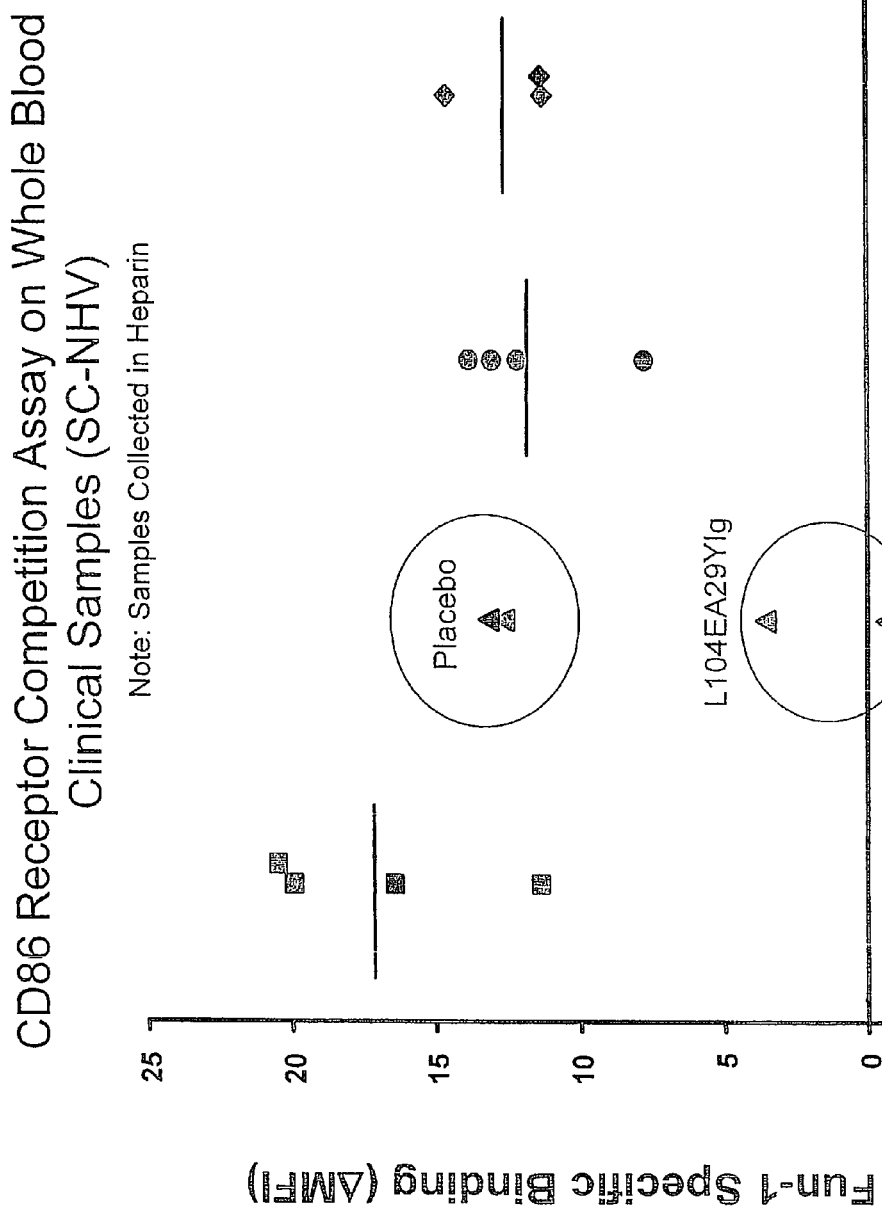
FIG. 8 depicts a CD86 receptor competition assay on whole blood collected from NHVs administered L104EA29YIg subcutaneously. (SC=Sub-cutaneous; squares indicate pre-dose, triangles indicate Day 5, circles indicate Day 14, and diamonds indicate Day 42).
Figure 9:
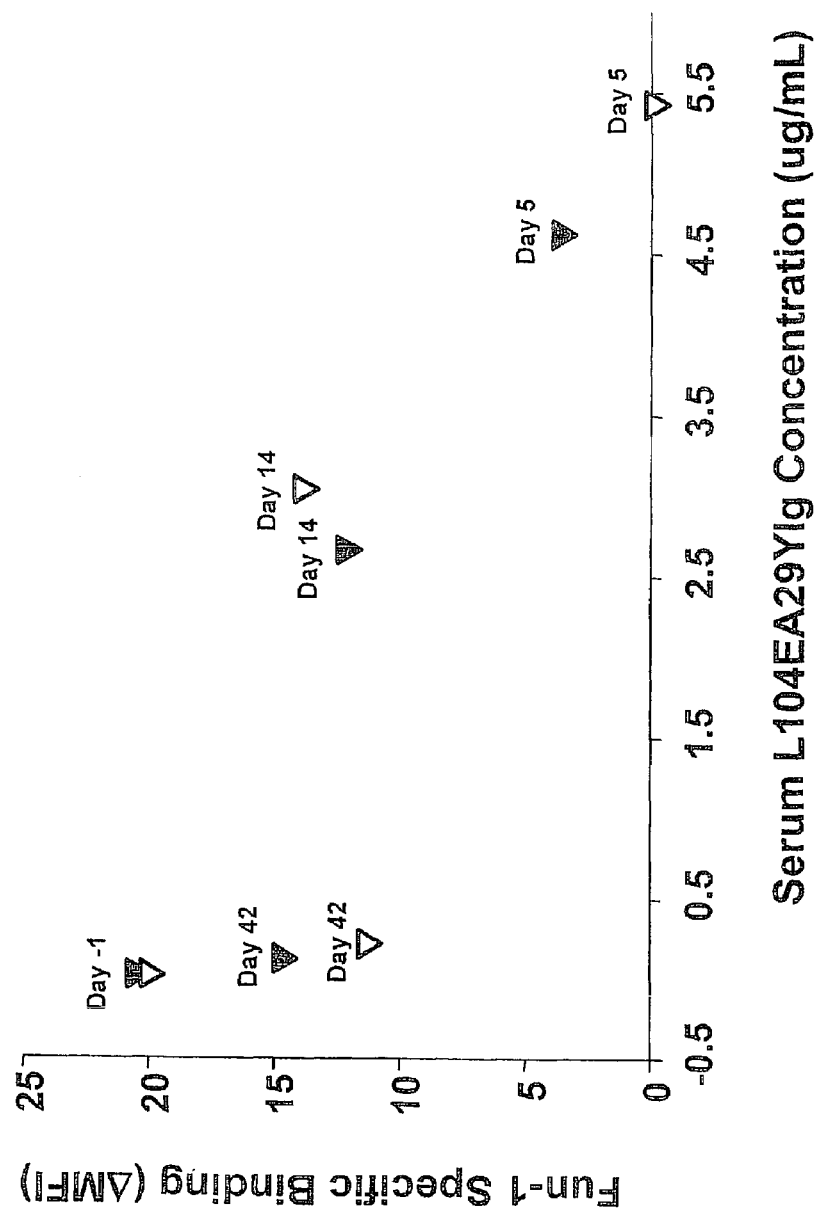
FIG. 9 depicts the correlation between pharmacokinetics (PK) and pharmacodynamics (PD) of the results shown in FIG. 8, which helps one understand what serum drug concentrations are required to achieve a desired pharmacodynamic activity such as saturating the target. Open and closed triangles represent the two subjects who received L104EA29YIg. This figure demonstrates that in the subjects administered L104EA29YIg SC, more inhibition of Fun-1 binding to peripheral blood monocytes is observed with increasing serum concentrations of L104EA29YIg.
Figure 11:
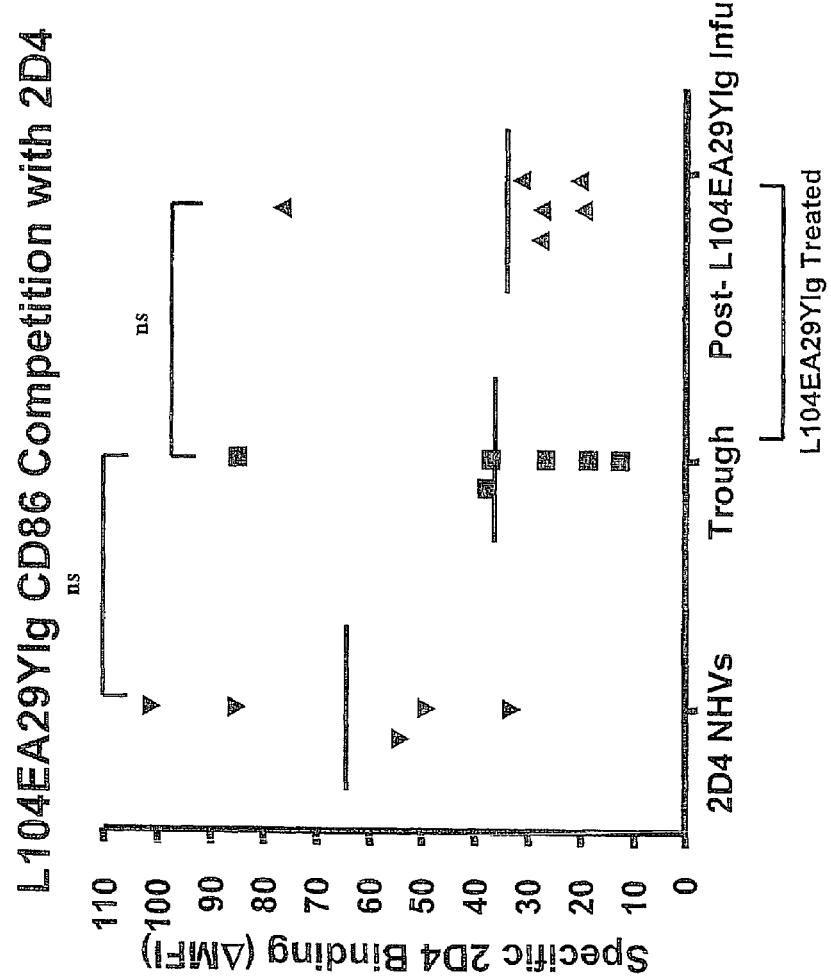
FIG. 11 depicts specific binding of mAb 2D4 in clinical samples (including blood from renal transplant patients treated with L104E29YIg). In transplant patients receiving L104EA29YIg, 2D4 binding is unchanged following administration of L104EA29YIg and not significantly different from NHVs.
Figure 12:
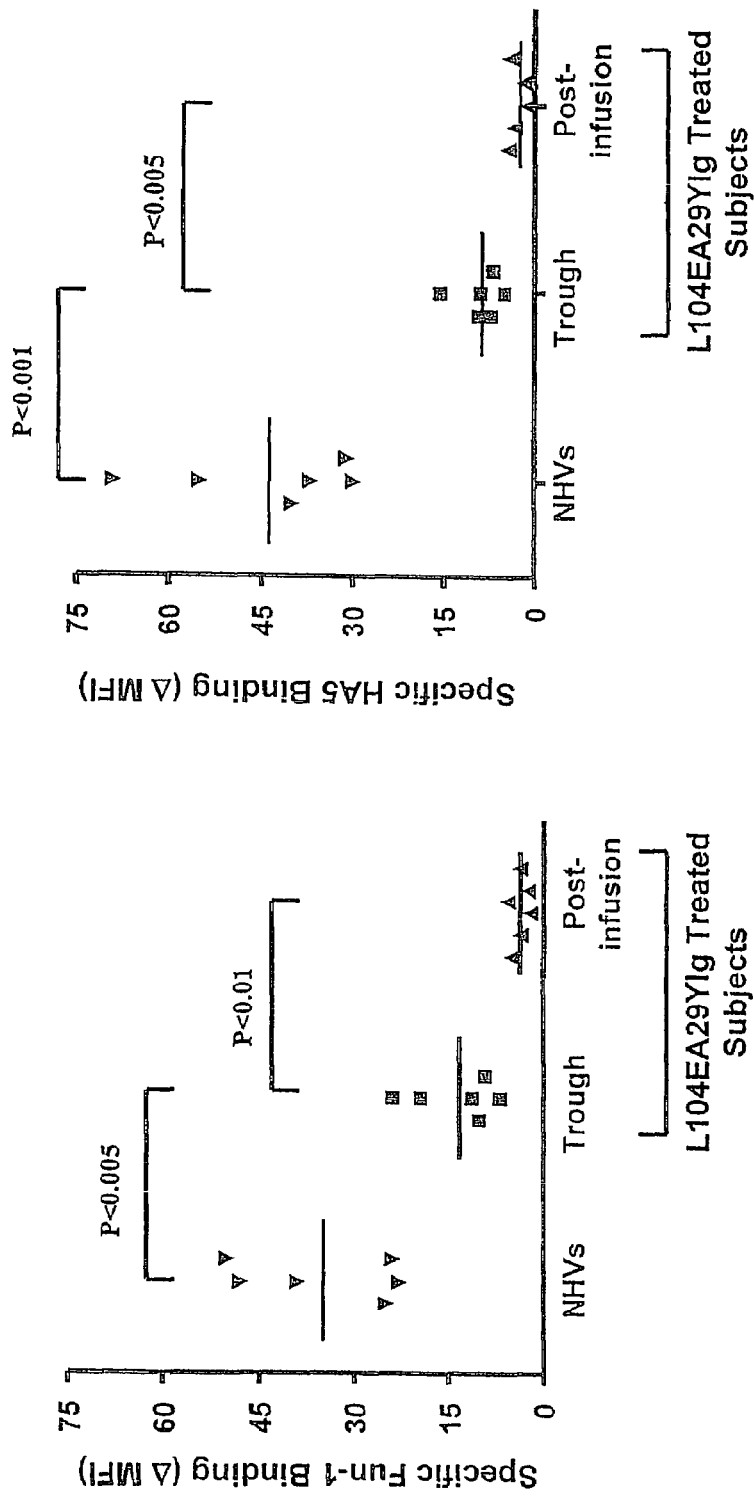
FIG. 12 depicts specific binding of mAb HA5 and mAb FUN1 in clinical samples (including blood from renal transplant patients treated with L104E29YIg). This data demonstrates that as opposed to 2D4, FUN-1 and HA5 binding are significantly inhibited by L104E29YIg administration in transplant patients and significantly reduced compared to NHVs.
Figure 13:
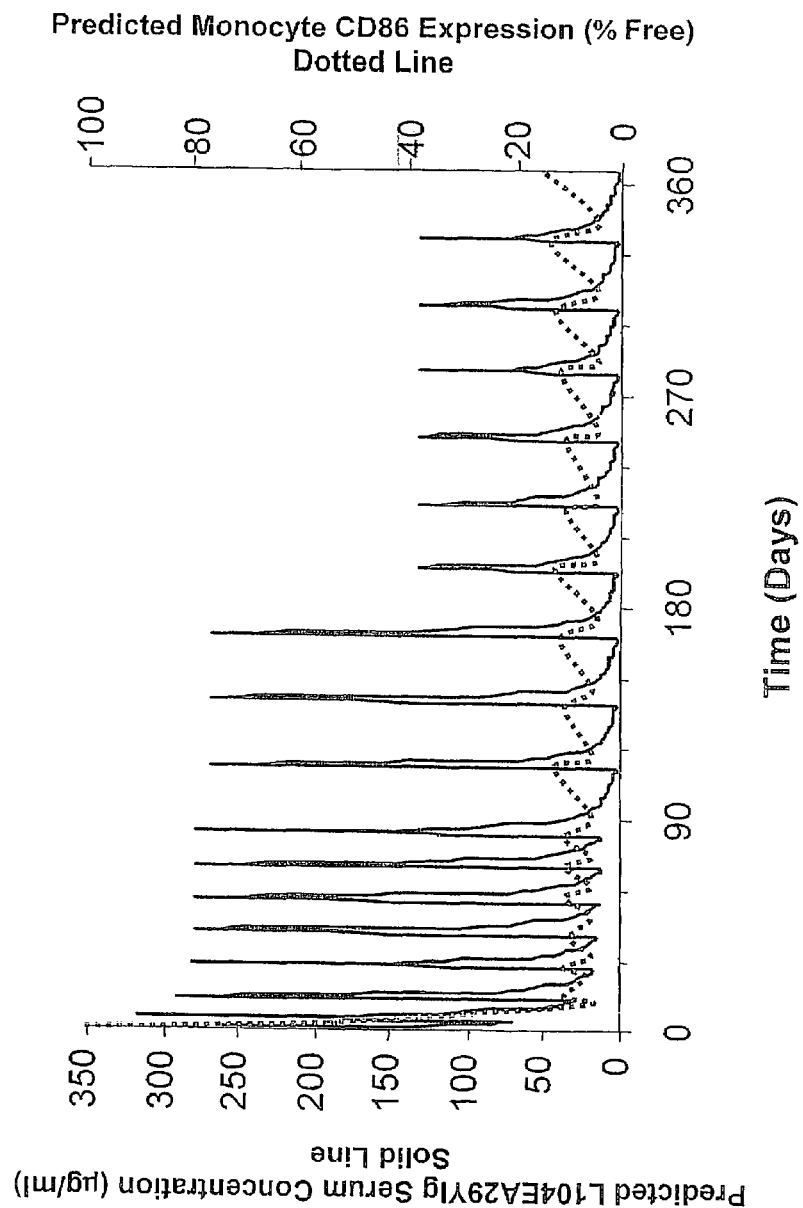
FIG. 13 depicts simulated clinical PK and PD profiles. This figure depicts a model suggesting how this assay could be used to monitor receptor saturation following L104E29YIg administration. It hypothesizes that shortly after the first dose, receptor saturation is maximized and remains at the desired level despite changes in dose regimen such as frequency of dose or strength of dose.

In clinical studies, FUN-1 specific binding, as measured by change in median fluorescence intensity (MFI), is inhibited substantially by Day 5 after dosing with L104EA29YIg. (See FIG. 8). L104EA29YIg inhibits binding of FUN-1, and, when administered subcutaneously, as the concentration of L104EA29YIg increases, so does the inhibition of FUN-1 binding. (See FIG. 9). In transplant patients continually receiving L104EA29YIg, 2D4 binding is unchanged following a single administration of L104EA29YIg and not significantly different from NHVs. (See FIG. 11). The term "trough" refers to the time point just prior to the next administration of the drug, when the concentration of drug is at its lowest blood level in a patient. As opposed to 2D4, Fun-1 and HA5 binding are significantly inhibited by L104EA29YIg administration in transplant patients and significantly reduced compared to NHVs. (See FIG. 12; 2D4 data not shown.) FIG. 13 is a model suggesting how this assay could be used to monitor receptor saturation following L104EA29YIg administration. It hypothesizes that shortly after the first dose, receptor saturation is maximized and remains at the desired level despite changes in dose regimen such as frequency of dose or strength of dose.

Not wishing to be bound by any specific procedure, the Applicants provide the following example procedure to demonstrate how the assay may be done:

Materials
L104EA29YIg, BMS Syracuse, lot 4E82288/MSF521A; 100 mg vial reconstituted with 10 ml PBS, to a final concentration of 10 mg/ml. 50 µl aliquots stored @-20° C.

CD86 PE (clone HA5.2B7) Beckman Coulter #IM2729 lot 15 (conc 6.25 µg/ml)
CD86 APC clone 2D4; 0.09 mg/ml; BMS generated mAb, APC conjugated by Calbiochem
CD14 FITC BD #555397
Purified anti-CD86 (clone HA5.2B7) Beckman Coulter #IM2728, 200 µg lyophilized; resuspended at 200 µg/ml in dH$_2$O/0.1% azide
Purified anti-human CD86 (clone 2D4) 2.29 mg/ml
Mouse IgG, reagent grade, Sigma #I5381; 10 mg lyophilized; resuspend in 5 ml PBS to a final concentration of 2 mg/ml, stored @4° C.
FACS Lysing Solution, 10×, BD #349202

Whole Blood In Vitro Procedure
1. Draw blood into ACD-A vacutainer or syringe with ACD-A as anti-coagulant.
2. Dilute 10 mg/ml L104EA29YIg in PBS to a concentration that is 10-fold above the desired final concentration. See dilutions in Table 1 below.

TABLE 1

Concentration of L104EA29YIg used in Assays

| L104EA29YIg final conc. | µl PBS | µl 10 mg/ml L104EA29YIg | Correlation with clinical values |
|---|---|---|---|
| 250 µg/ml | 150 | 50 | peak |
| 125 µg/ml | 175 | 25 | intermediate |
| 5 µg/ml | 100 | First dilute 1:100, then add 100 | trough |
| 2 µg/ml | 160 | First dilute 1:100, then add 40 | trough |

3. Dispense 150 µl of diluted L104EA29YIg into a 12×75 mm polypropylene tube. Dispense 150 µl PBS to additional tube for untreated control.
4. Add 1.35 ml of whole blood to L104EA29YIg or PBS. Incubate on a rotator in the 37° C. CO$_2$ incubator for 1 hr.
5. On ice, dispense 10 µl of mouse IgG solution to 12×75 mm polystyrene sample tubes.
6. Dispense 100 µl of blood for each sample into 12-12×75 polystyrene tubes.
7. Incubate on ice 10 minutes.
8. To three tubes, add 3.5 µl purified, unlabeled HA5 mAb (purified). To three additional tubes, add 4.4 µl of purified, unlabeled 2D4 mAb. (See table below). Incubate 15 minutes on ice.
9. To all tubes, add 10 µl CD14 FITC.
10. Add 20 µl of anti-human CD86 PE (clone HA5.2B7) antibody to tubes as indicated in table below. Add 10 µl of 2D4-APC to tubes as indicated in Table 2 below.

TABLE 2

Addition of unlabeled/labeled antibody reagents.

| TUBE | HA5 PE, µl | Unlabeled HA5, µl | 2D4-APC, µl | Unlabeled 2D4, µl | CD14-FITC, µl |
|---|---|---|---|---|---|
| 1 | 20 | — | — | — | 10 |
| 2 | 20 | — | — | — | 10 |
| 3 | 20 | — | — | — | 10 |
| 4 | 20 | 3.5 | — | — | 10 |
| 5 | 20 | 3.5 | — | — | 10 |
| 6 | 20 | 3.5 | — | — | 10 |
| 7 | — | — | 10 | — | 10 |
| 8 | — | — | 10 | — | 10 |
| 9 | — | — | 10 | — | 10 |
| 10 | — | — | 10 | 4.4 | 10 |
| 11 | — | — | 10 | 4.4 | 10 |
| 12 | — | — | 10 | 4.4 | 10 |

11. Incubate 30 minutes on ice.
12. Dilute 10×FACS Lysing Solution 1:10 with dH$_2$O. Add 1 ml of FACS Lysing Solution to each tube. Vortex and incubate RT 15 minutes.
13. Spin the tubes for 5 minutes at 1500 rpm, at 4° C.
14. Resuspend in 200 µl FACS Lysing Solution.
15. Read on flow cytometer, adjusting compensation settings as necessary. For acquisition, gate on the monocyte population, as identified by forward and side scatter properties (G1). Gate on CD14+ monocytes using a dot plot of forward scatter vs. CD14 (G2). The additive events of G1 and G2 (termed G3) are observed on a histogram looking at the FL2 channel (CD86 PE, FUN1) or FL4 channel (CD86 APC, 2D4). Acquisition is stopped after accumulation of 3000 G3 events.
16. For analysis, the median fluorescence of G3 events is determined on a histogram of FL2 events (CD86 PE, HA5) or FL4 events (CD86 APC, 2D4) and is used to determine the relative level of CD86 present on the surface of CD14+ monocytes.

Example 3

Clinical Assay

A. CD86 Clinical Assay Procedure

To perform such an assay, blood samples obtained from patients dosed with L104EA29YIg can be aliquoted into 200 µl samples into a 12×75 mm polystyrene tube on ice (4° C.). To each tube, 25 µg of mouse mixed IgGs can be added to block potential FcR binding of detection antibodies (e.g. FUN-1, 2D4, 1420 etc.) and incubated for 15 minutes at 4C. To each tube, 20 µl anti-human CD14 FITC can be added and indicated amount (e.g. 1 µg) of fluorescently labeled anti-human CD86 (e.g. FUN1, HA5 or 2D4) and incubated at 4° C. for 30 minutes. To assess non-specific fluorescence associated with the labeled anti-CD86 mAbs, excess unlabeled anti-human CD86 mAb is added to a subset of the relevant samples (e.g. unlabeled HA5 is added to samples containing labeled HA5). 2 ml of FACS Lysing Solution (BD) can be added to each tube to lyse the red blood cells and fix the leukocytes. The blood may be subsequently incubated at 4° C. for 30 minutes. To isolate the leukocytes and remove lysed RBCs and excess reagents, the samples can be centrifuged at 1500 rpm for 5 minutes at 4° C. and resuspended in 200 µl FACS Lysing Solution for analysis on the flow cytometer as described in the methods. The total CD86 expressed on the surface of the APC can be determined by using mAb 2D4 while the available CD86 can be measured by using mAb FUN-1 or HA5 as examples. Specific binding (ΔMFI) is determined by the difference between the total binding (labeled anti-CD86 mAb alone) and the non-specific binding (labeled +excess unlabeled anti-CD86 mAb). With this data one could calculate the ratio of unbound CD86 to total CD86 and determine the extent of receptor saturation by L104EA29YIg in a given blood sample. Alternatively, one could also perform the same procedure on patient blood obtained prior to administration of L104EA29YIg to determine the total CD86 levels and repeat the analysis following administration of the compound to measure the decrease in the binding of the competing antibody as compared to pre-treatment. In this way, one would be able to determine the extent of receptor saturation following administration of compound.

B. CD80 Clinical Assay Procedure

Although CD80 expression on monocytes is very low or not at all, other cell types or activated monocytes do express higher levels of CD80. The expression of total and available CD80 can be measured in a similar fashion on these cell types by using the non competing CD80 mAb 1420 to measure total CD80 expressed and the competing mAb L307.4 or mAb MAB104 to measure CD80 unbound by L104EA29YIg. With this data one could calculate the ratio of unbound CD80 to total CD80 and determine the extent of receptor saturation by L104EA29YIg in a given blood sample. Alternatively, one could also perform the same procedure on patient blood obtained prior to administration of L104EA29YIg to determine the total CD80 levels and repeat the analysis following administration of the compound to measure the decrease in the binding of the competing antibody as compared to pre-treatment. In this way, one would be able to determine the extent of receptor saturation following administration of compound.

Figure 20:
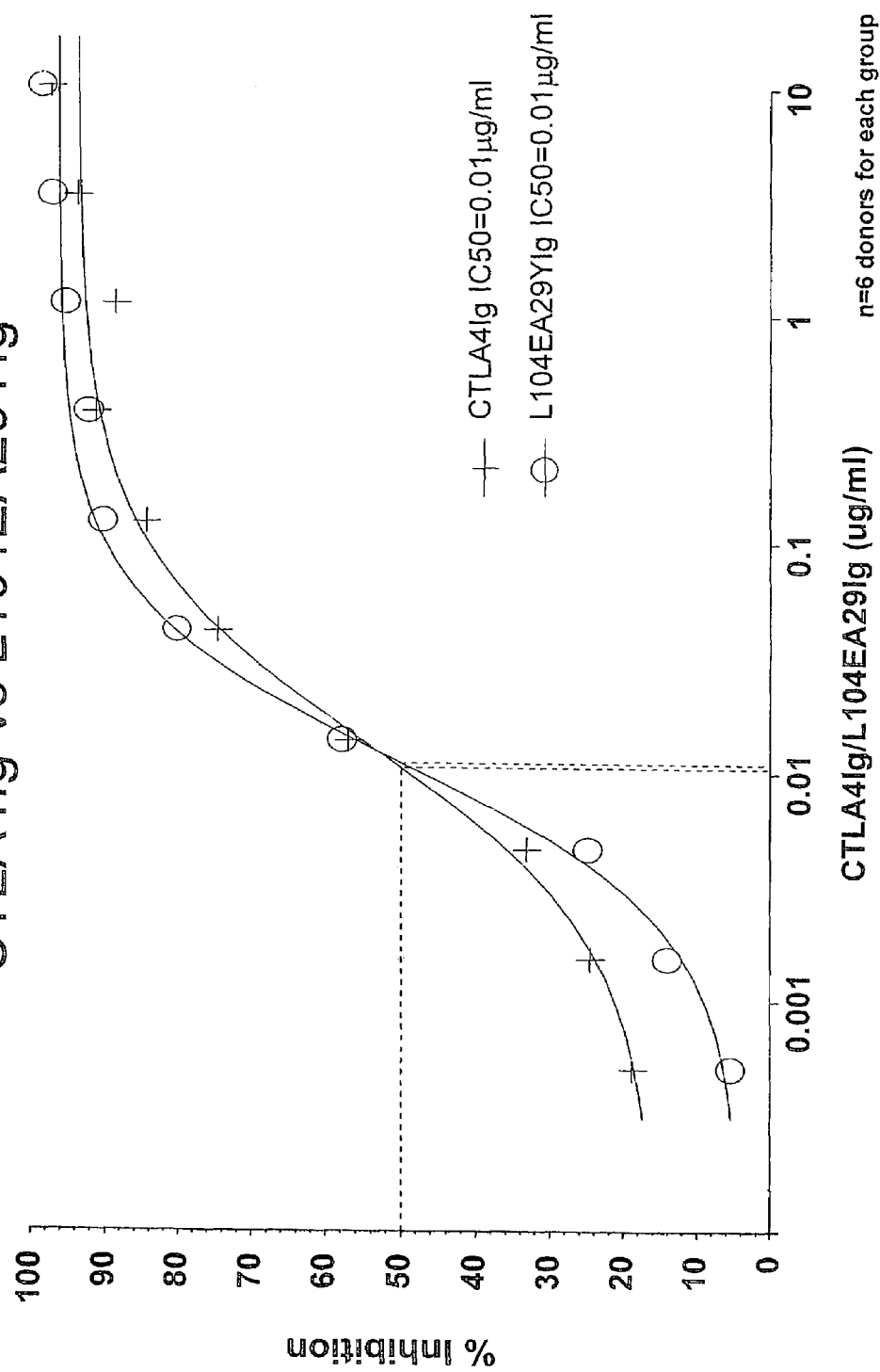
FIG. 20 depicts CD80 receptor competition assay in whole blood from normal healthy volunteers with mAb L307.4. The data demonstrate that the concentration of CTLA4Ig required to inhibit specific binding of L307.4 by 50% is 0.01 μg/ml, and the concentration of L104EA29YIg required to inhibit specific binding of L307.4 by 50% is 0.01 μg/ml. The results represent the average response of 6 donors.

As shown in FIG. 20, whole blood was stimulated with 1 µg/ml LPS for 4 hours at 37° C. to induce the expression of CD80. The unbound CD80 level was determined by the level of binding of competing antibody L307.4. The results shown in FIG. 20 represent the average response of 6 donors.

C. Allo-Response Assay

Figure 21:
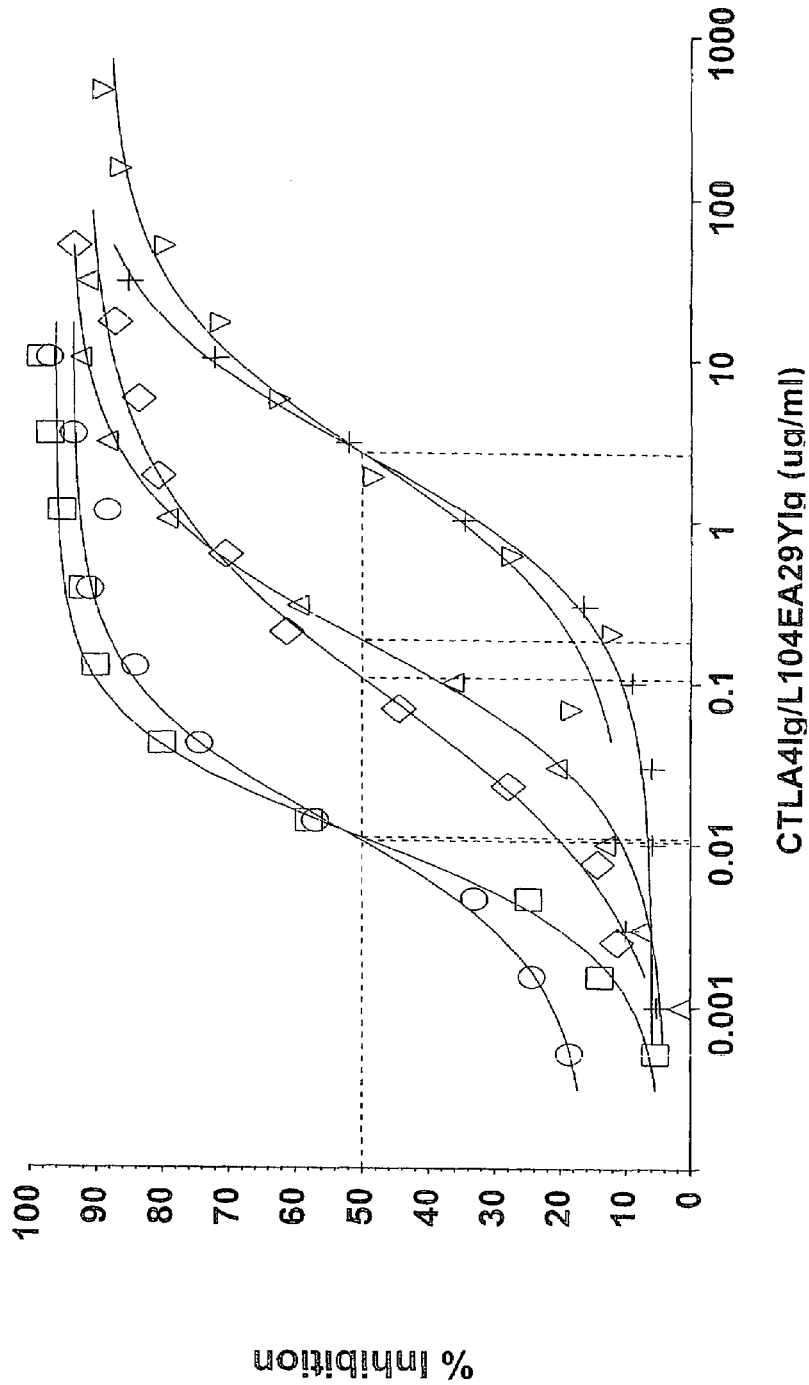
FIG. 21 depicts the results of CD80 and CD86 receptor saturation and inhibition of allo-response assay for comparison. Depicted are the IC50s of CTLA4Ig in a mixed leukocyte reaction, in a CD86 receptor competition assay using mAb HA5, and in a CD80 receptor competition assay using mAb L307.4. Also depicted are the IC50s of L104EA29YIg in a mixed leukocyte reaction, in a CD86 receptor competition assay, and in a CD80 receptor competition assay.

To measure allo-responses, mixed leukocyte reactions (MLR) were performed. For MLR proliferation assays measuring titrations of CTLA-4Ig or L104EA29YIg, T cells were cultured at $1 \times 10^5$/well in quadruplicate wells together with $1 \times 10^4$, $2 \times 10^3$ or $0.4 \times 10^3$ allogeneic MoDC as antigen-presenting cells (APCs) in 96-well round-bottom plates in a total volume of 200 µl of 10% FCS-RPMI. CTLA-4Ig or L104EA29YIg was added to wells at a starting final concentration of 30 µg/ml, followed by half-log dilutions down to a final concentration of 1 ng/ml. On day 5 after initiation of the MLR, cultures were pulsed with one µCi of $^3$[H]-thymidine (PerkinElmer, Boston, Mass.) for 6 hours, harvested on a Packard cell harvester (PerkinElmer), and counted by liquid scintillation on a +Packard TopCount NXT (PerkinElmer). The results of CD80 and CD86 receptor saturation and inhibition of allo-response assay are shown in FIG. 21.

Example 4

Methods of Producing Antibodies

The production of antibodies is discussed in detail in U.S. patent application Ser. No. 10/375157 (Publication No. 2003-0224458) which is hereby incorporated by reference in its entirety. The antibodies of the invention can be produced by any method known in the art for the synthesis of antibodies, in particular, by chemical synthesis or preferably, by recombinant expression techniques.

The mAb 2D4 and mAB 1420 were labeled with fluorochromes typically used in flow cytometry studies (FITC, PE, etc.). The assay is not dependent on the type of fluorochrome used, different labels can be used in this assay and mixed and matched to suit the investigators purpose.

Throughout this application various publications are referenced. The disclosures of these publications in their entireties are hereby incorporated by reference into this application in order to more fully describe the state of the art to which this invention pertains.

What is claimed is:

1. An assay method for monitoring binding efficiency of L104EA29YIg to CD80 or CD86 receptor in a patient, said method comprising the steps of:
   (a) obtaining a blood sample from a patient dosed with L104EA29YIg, the blood sample including leukocyte cells;
   (b) adding CD14-FITC to the blood sample;
   (c) adding labeled competing anti-receptor antibody selected from the group consisting of mAb FUN-1, mAb IT2.2, mAb HA5.2B7, mAb L307.A and mAb MAB 104 and non-competing anti-receptor antibody selected from the group consisting of mAb 2D4 and mAb 1420 to the blood sample;
   (d) lysing the blood sample and fixing leukocytes;
   (e) isolating leukocytes from the lysed blood sample;
   (f) measuring the total receptor expression and available receptor from the leukocyte cells.

2. The assay of claim 1, wherein the receptor is CD86.

3. The assay of claim 2, wherein the competing anti-receptor antibody is mAb FUN-1.

4. The assay of claim 2, wherein the competing anti-receptor antibody is mAb IT2.2.

5. The assay of claim 2, wherein the competing anti-receptor antibody is mAB HA5.2B7.

6. The assay of claim 2, wherein the non-competing anti-receptor antibody is mAb 2D4.

7. The assay of claim 1, wherein the receptor is CD80.

8. The assay of claim 7, wherein the competing anti-receptor antibody is mAb L307.4.

9. The assay of claim 7, wherein the competing anti-receptor antibody is mAb MAB104.

10. The assay of claim 7, wherein the non-competing anti-receptor antibody is mAb 1420.

11. The assay of claim 1, further comprising detecting the presence of antibodies using flow cytometry.

12. The assay of claim 1, wherein subsequent to step (a) and prior to step (b), further comprising step (a') blocking Fc receptor-mediated non-specific binding.

13. The assay of claim 12, wherein the Fc receptor-mediated non-specific binding is blocked by the addition of mixed mouse IgGs to the blood sample.

14. The assay of claim 1, wherein the binding efficiency of L104EA29YIg is measured by comparing bound and unbound receptors to determine percent of receptor saturation by L104EA29YIg.

15. An assay method for monitoring binding efficiency of L104EA29YIg to CD80 or CD86 receptor in a patient, said method comprising the steps of:
   (a) obtaining a control blood sample from said patient;
   (b) dosing said patient with L104EA29YIg,
   (c) obtaining a test blood sample from said patient dosed with L104EA29YIg;
   (d) adding CD14-FITC to the control and test blood samples;
   (e) adding labeled competing anti-receptor antibody selected from the group consisting of mAb FUN-1, mAb IT2.2, mAb HA5.2B7, mAb L307.A and mAb MAB 104 to the control and test blood samples;
   (f) lysing the blood samples and fixing leukocytes;
   (g) isolating leukocytes from the lysed blood sample;
   (h) comparing the binding of the competing anti-receptor antibody in test and control isolated leukocytes.

16. The assay of claim 15, wherein the receptor is CD86.

17. The assay of claim 16, wherein the competing anti-receptor antibody is mAb FUN-1.

18. The assay of claim 16, wherein the competing anti-receptor antibody is mAb IT2.2.

19. The assay of claim 16, wherein the competing anti-receptor antibody is mAb HA5.2B7.

20. The assay of claim 15, wherein the receptor is CD80.

21. The assay of claim 20, wherein the competing anti-receptor antibody is mAb L307.4.

22. The assay of claim 20, wherein the competing anti-receptor antibody is mAb MAB104.

23. The assay of claim 14, further comprising detecting the presence of antibodies using flow cytometry.

* * * * *

UNITED STATES PATENT AND TRADEMARK OFFICE
CERTIFICATE OF CORRECTION

PATENT NO. : 7,510,844 B2 Page 1 of 1
APPLICATION NO. : 11/656206
DATED : March 31, 2009
INVENTOR(S) : Robert M. Townsend, Catherine A. Fleener and Francisco Leon It is certified that error appears in the above-identified patent and that said Letters Patent is hereby corrected as shown below:

In the Claims:

Claim 1
Column 23 Line 11
L307.A should read "L307.4"

Claim 15
Column 24 Line 19
L307.A should read "L307.4"

Signed and Sealed this

Fourth Day of August, 2009

JOHN DOLL
*Acting Director of the United States Patent and Trademark Office*

SEQUENCE LISTING

<160> NUMBER OF SEQ ID NOS: 4

<210> SEQ ID NO 1
<211> LENGTH: 1152
<212> TYPE: DNA
<213> ORGANISM: artificial sequence
<220> FEATURE:
<223> OTHER INFORMATION: CTLA4Ig

<400> SEQUENCE: 1

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacctg ggcataggca acggaaccca gatttatgta     420
attgatccag aaccgtgccc agattctgat caggagccca aatcttctga caaaactcac     480
acatccccac cgtcccagc acctgaactc ctggggtgga cgtcagtctt cctcttcccc     540
ccaaaaccca aggacaccct catgatctcc cggacccctg aggtcacatg cgtggtggtg     600
```

-continued

```
gacgtgagcc acgaagaccc tgaggtcaag ttcaactggt acgtggacgg cgtggaggtg    660
cataatgcca agacaaagcc gcgggaggag cagtacaaca gcacgtaccg ggtggtcagc    720
gtcctcaccg tcctgcacca ggactggctg aatggcaagg agtacaagtg caaggtctcc    780
aacaaagccc tcccagcccc catcgagaaa accatctcca agccaaagg gcagccccga     840 gaaccacagg tgtacaccct gcccccatcc cgggatgagc tgaccaagaa ccaggtcagc    900
ctgacctgcc tggtcaaagg cttctatccc agcgacatcg ccgtggagtg ggagagcaat    960
gggcagccgg agaacaacta caagaccacg cctcccgtgc tggactccga cggctccttc   1020
ttcctctaca gcaagctcac cgtggacaag agcaggtggc agcaggggaa cgtcttctca   1080
tgctccgtga tgcatgaggc tctgcacaac cactacacgc agaagagcct ctccctgtct   1140
ccgggtaaat ga                                                       1152
```

<210> SEQ ID NO 2
<211> LENGTH: 383
<212> TYPE: PRT
<213> ORGANISM: artificial sequence
<220> FEATURE:
<223> OTHER INFORMATION: CTLA4Ig

<400> SEQUENCE: 2

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
        50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255
```

-continued

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 3
<211> LENGTH: 1152
<212> TYPE: DNA
<213> ORGANISM: artificial sequence
<220> FEATURE:
<223> OTHER INFORMATION: L104EA29YIg

<400> SEQUENCE: 3

| | | |
|---|---|---|
| atgggtgtac tgctcacaca gaggacgctg ctcagtctgg tccttgcact cctgtttcca | 60 |
| agcatggcga gcatggcaat gcacgtggcc cagcctgctg tggtactggc cagcagccga | 120 |
| ggcatcgcta gctttgtgtg tgagtatgca tctccaggca aatatactga ggtccgggtg | 180 |
| acagtgcttc ggcaggctga cagccaggtg actgaagtct gtgcggcaac ctacatgatg | 240 |
| gggaatgagt tgaccttcct agatgattcc atctgcacgg gcacctccag tggaaatcaa | 300 |
| gtgaacctca ctatccaagg actgagggcc atggacacgg actctacat ctgcaaggtg | 360 |
| gagctcatgt acccaccgcc atactacgag ggcataggca acggaaccca gatttatgta | 420 |
| attgatccag aaccgtgccc agattctgat caggagccca atcttctga caaaactcac | 480 |
| acatccccac cgtccccagc acctgaactc ctggggggat cgtcagtctt cctcttcccc | 540 |
| ccaaaaccca aggacaccct catgatctcc cggacccctg aggtcacatg cgtggtggtg | 600 |
| gacgtgagcc acgaagaccc tgaggtcaag ttcaactggt acgtggacgg cgtggaggtg | 660 |
| cataatgcca agacaaagcc gcgggaggag cagtacaaca gcacgtaccg tgtggtcagc | 720 |
| gtcctcaccg tcctgcacca ggactggctg aatggcaagg agtacaagtg caaggtctcc | 780 |
| aacaaagccc tcccagcccc catcgagaaa accatctcca agccaaagg cagccccga | 840 |
| gaaccacagg tgtacaccct gcccccatcc cgggatgagc tgaccaagaa ccaggtcagc | 900 |
| ctgacctgcc tggtcaaagg cttctatccc agcgacatcg ccgtggagtg ggagagcaat | 960 |
| gggcagccgg agaacaacta caagaccacg cctcccgtgc tggactccga cggctccttc | 1020 |
| ttcctctaca gcaagctcac cgtggacaag agcaggtggc agcaggggaa cgtcttctca | 1080 |
| tgctccgtga tgcatgaggc tctgcacaac cactacacgc agaagagcct ctccctgtct | 1140 |
| ccgggtaaat ga | 1152 |

<210> SEQ ID NO 4
<211> LENGTH: 383
<212> TYPE: PRT
<213> ORGANISM: artificial sequence -continued

```
<220> FEATURE:
<223> OTHER INFORMATION: L104EA29YIg

<400> SEQUENCE: 4

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380
```